(12) United States Patent
Schmitt

(10) Patent No.: US 9,086,366 B2
(45) Date of Patent: Jul. 21, 2015

(54) DETERMINING A MATERIAL PROPERTY BASED ON SCATTERED RADIATION

(71) Applicant: L-3 Communications Security and Detection Systems, Inc., Woburn, MA (US)

(72) Inventor: Michael H. Schmitt, Billerica, MA (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 165 days.

(21) Appl. No.: 13/766,239

(22) Filed: Feb. 13, 2013

(65) Prior Publication Data

US 2013/0208850 A1  Aug. 15, 2013

Related U.S. Application Data

(60) Provisional application No. 61/599,197, filed on Feb. 15, 2012.

(51) Int. Cl.
*G01N 23/201* (2006.01)
*G01N 23/20* (2006.01)

(52) U.S. Cl.
CPC .............. *G01N 23/20* (2013.01); *G01N 23/201* (2013.01); *G01N 2223/051* (2013.01); *G01N 2223/054* (2013.01)

(58) Field of Classification Search
CPC .................. G01N 23/20066; G01N 23/20083; G01N 23/20; G01N 23/203; G01N 2223/051; G01N 2223/053; G01N 2223/054; G01N 2223/055; G01N 2223/063
See application file for complete search history.

(56) References Cited

U.S. PATENT DOCUMENTS

| | | | |
|---|---|---|---|
| 6,226,352 B1 | 5/2001 | Salb | |
| 2003/0016783 A1* | 1/2003 | Grodzins et al. | 378/57 |
| 2007/0019788 A1 | 1/2007 | Ledoux et al. | |
| 2008/0008292 A1 | 1/2008 | Krmar et al. | |
| 2009/0060124 A1 | 3/2009 | Grass et al. | |
| 2010/0002834 A1 | 1/2010 | Gudmundson et al. | |

FOREIGN PATENT DOCUMENTS

JP  2006170652 A  6/2006

OTHER PUBLICATIONS

Morgan, H.M., et al., "Gamma-Ray Scattering for Mandibular Bone Density Measurement," The British Journal of Radiology, 72 (1999), pp. 1069-1072.
Puumalainen, P., et al., "A Coherent/Compton Scattering Method Employing an X-Ray Tube for Measurement of Trabecular Bone Mineral Content," Phys. Med. Biol., 1982, vol. 27, No. 3, pp. 425-429.
Stalp, John T., and Mazess, Richard B., "Determination of Bone Density by Coherent-Compton Scattering," Med. Phys. 7(6), Nov./Dec. 1980, pp. 723-726.
International Search Report and Written Opinion for International Application No. PCT/US2013/026055, mailed Apr. 19, 2013.

* cited by examiner

*Primary Examiner* — Glen Kao
(74) *Attorney, Agent, or Firm* — Fish & Richardson P.C.

(57) ABSTRACT

Radiation is directed at an object, and radiation scattered by the object is sensed. An angular distribution of scatter in the sensed scattered radiation relative to a path of the radiation directed at the object is determined, and the angular distribution is evaluated. One or more atomic numbers, or effective atomic numbers, of materials composing the object is determined based on evaluating the angular distribution.

31 Claims, 20 Drawing Sheets

DETERMINING A MATERIAL PROPERTY BASED ON SCATTERED RADIATION

TECHNICAL FIELD

This disclosure relates to determining a material property based on scattered radiation.

BACKGROUND

Characteristics of a material may be determined based on the interaction of the material with x-ray radiation.

SUMMARY

In one general aspect, radiation is directed at an object. Radiation scattered by the object is sensed. An angular distribution of scatter in the sensed scattered radiation relative to a path of the radiation directed at the object is determined. The angular distribution is evaluated. One or more atomic numbers, or effective atomic numbers, of materials composing the object is determined based on evaluating the angular distribution.

Implementations may include one or more of the following features. For example, evaluating the angular distribution may include determining a ratio of scatter at two angles. Sensing radiation scattered by the object may include one or more of measuring x-ray fluency, measuring x-ray energy deposited on a detector, or measuring the x-ray fluency and a per-photon energy. Determining the one or more atomic numbers, or effective atomic numbers, of materials composing the object may include determining the one or more atomic numbers, or effective atomic numbers, of materials composing the object based on the ratio of scatter at two angles. Sensing radiation scatter by the object may include sensing scattered x-ray radiation at a first angle relative to the path of the radiation directed at the object, the radiation directed at the object being x-ray radiation, and sensing scattered x-ray radiation at a second angle relative to the path of the x-ray beam incident upon the object, the first and second angles being different. The first angle may indicate a coherent scattering angle, and the second angle may indicate an incoherent scattering angle. The second angle may be greater than the first angle.

The object may be a homogeneous object that includes a first side and a second side. Sensing scattered x-ray radiation at the first angle may include sensing scattered x-ray radiation on the first side of the object. Sensing scattered x-ray radiation at the second angle may include sensing scattered x-ray radiation on the second side of the object.

In some implementations, sensing radiation scattered by the object may include sensing scattered radiation at two or more distinct angles relative to the path of the radiation that is directed at the object. Sensing radiation scattered by the object may include sensing radiation scattered at more than 10 distinct angles. The angles may be between about 0 and 180 degrees relative to the path of the radiation directed at the object. Sensing radiation scattered by the object may include sensing radiation scattered at more than 30 distinct angles. The angles may be between about 0 and 180 degrees relative to the path of the radiation directed at the object. A single detector may move relative to the object to sense the scattered radiation at each of the two or more angles. Sensing scattered radiation may include sensing, at a single detector, first scattered radiation when a source is in a first position relative to the object, and second scattered radiation when the source is in a second position relative to the object. The first and second positions may be different. The first and second scattered radiation may be scattered at different angles. A collimator may be moved relative to the object, such that the scattered radiation may be sensed at the two or more distinct angles when the collimator moves to a position corresponding to the two or more distinct angles. The collimator may include a filter wheel. The collimator may include a translated opening.

In some implementations, directing radiation at an object may include generating at least two x-ray beams, and directing the at least two x-ray beams at the object. Each of the two x-ray beams may have a distinct energy. An amount of attenuation of the radiation caused by the object may be estimated. The estimated amount of attenuation may be accounted for prior to determining one or more atomic numbers, or effective atomic numbers, of materials composing the object. Estimating the amount of attenuation may be based on one or more of computed tomography, a transmission x-ray measurement, or a priori knowledge of a density of the object. A visual representation of the object may be presented.

In another general aspect, a system includes one or more detectors configured to sense radiation. The detectors are positioned to sense radiation scattered from an object. The system also includes an electronic memory coupled to a processor. The electronic memory includes instructions that, when executed, cause the processor to determine an angular distribution of scatter in the sensed scattered radiation relative to a path of the radiation directed at the object, evaluate the angular distribution, and determine one or more atomic numbers, or effective atomic numbers, of materials composing the object based on evaluating the angular distribution.

Implementations may include one or more of the following features. For example, one or more sources may be configured to produce radiation and direct the radiation towards the object. The one or more sources may be configured to move relative to the object. The one or more detectors may be configured to move relative to the object. The system may also include one or more collimating structures located in a path of the radiation scattered from the object.

Determining an angular distribution of scatter may include one or more of estimating a peak small angle scatter and a peak large angle scatter, estimating an amount of scatter within a range of angles in a small scattering angle region and an amount of scatter within a range of angles in a large scattering angle region, comparing a distribution of the sensed radiation to pre-determined tables, or fitting an angle-dependent distribution of the sensed radiation to a parameterization including both coherent and incoherent contributions. The detectors may be positioned to sense radiation scattered from an enclosure, the enclosure containing an object. The enclosure may be a container. The container may include a bottle. The enclosure may be a pipe, and the object may flow through the pipe. The enclosure may be a tunnel, and the object may travel through the tunnel along a conveyor belt.

In another general aspect, radiation is directed at an object. Radiation scattered by the object is sensed. An amount of coherent scatter and an amount of incoherent scatter in the sensed scattered radiation is determined. An atomic number, or effective atomic number, of material composing the object is determined based on the amount of coherent scatter and the amount of incoherent scatter.

Implementations of the techniques discussed above may include a method or process, a system or apparatus, a kit, method, and/or process for retrofitting an existing system, and/or computer software stored on a computer-readable storage medium.

DETAILED DESCRIPTION

Figure 1:
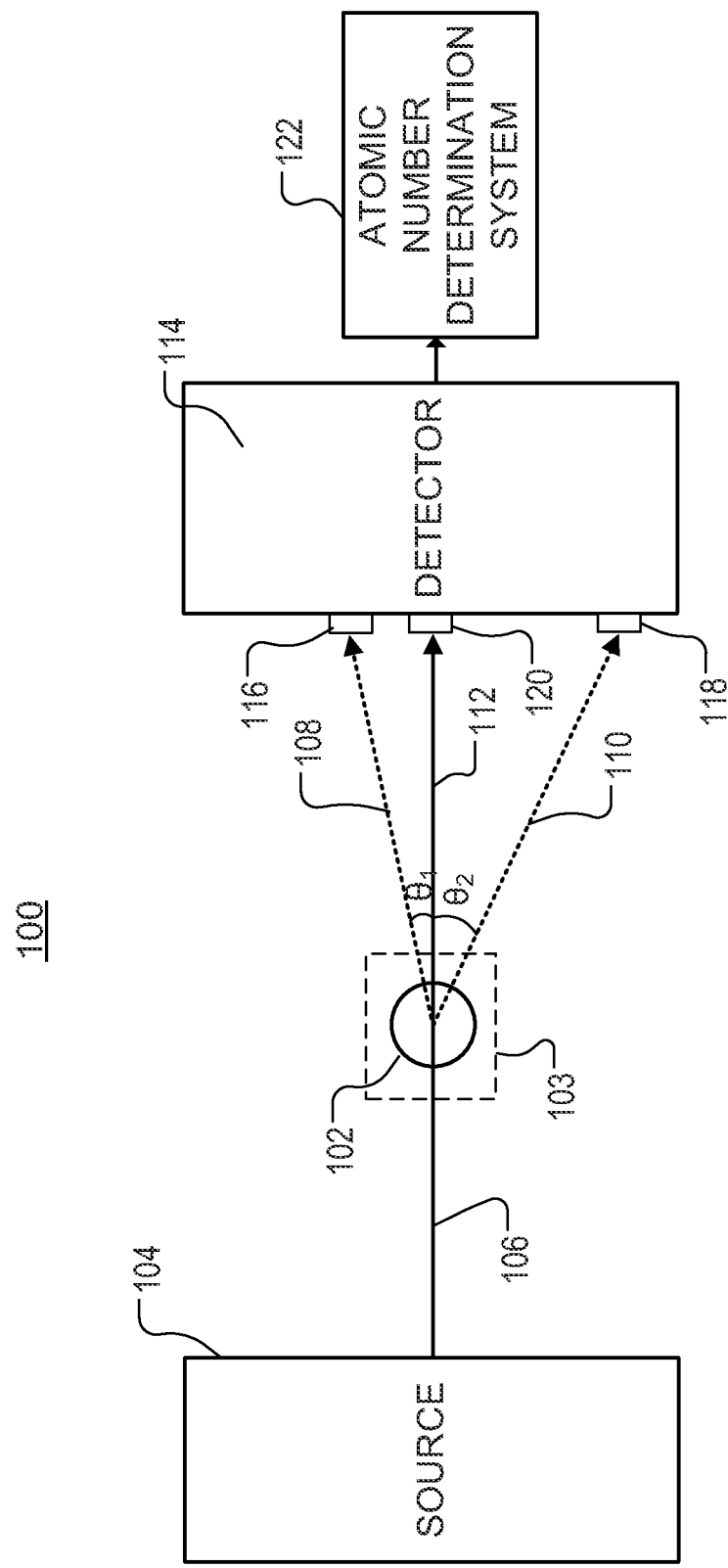
FIG. 1 is an illustration of an example system that determines a property of a material of an object.

An interaction between an object and an x-ray beam may produce coherent scatter (Rayleigh scatter) and/or incoherent scatter (Compton scatter). A figure of merit related to a material property of the object, such as an atomic number of a substance that makes up the object, may be determined by comparing an amount of coherent scatter from the object to an amount of incoherent scatter from the object. For example, the ratio (the scatter ratio) of an amount of coherent scatter to an amount of incoherent scatter may be used to determine the atomic number (Z) of the substance. For objects that include more than one elemental constituent, the ratio may be used to determine the effective atomic number ($Z_{eff}$) of the composite material that makes up the object. In the discussion below, atomic number (Z) refers to the atomic number of a single element and may be interchanged for effective atomic number ($Z_{eff}$), and vice versa, for objects composed generally of a single element. When more than one elemental constituent is present, the summation of contributions from coherent and incoherent scatter from each of the constituent elements may be used to determine one or more of the multiple unique atomic numbers (Z) composing the material that makes up the object. These multiple atomic number (Z) contributions which may be combined in a known way according to their relative concentration within the substance to produce a single effective atomic number ($Z_{eff}$).

The material of the object may be identified as a particular material, or type of material, from the one or more atomic numbers that make up the material. For example, the object could be identified as an object that is hazardous, or an explosive hidden among innocuous items in a bag. The object may be a portion of a homogeneous flow or a homogeneous object that is monitored non-destructively.

As discussed in greater detail below, by measuring an amount of radiation scattered by an object as a function of angle relative to the direction of propagation of the incident radiation (the scattering angle), the one or more atomic numbers of a material that makes up the object may be determined. The radiation described for exemplary purposes herein is x-ray radiation. However, any other suitable form of electromagnetic radiation may be used, such as, for example, gamma radiation. Alternatively, measuring the amount of scatter from an object as a function of x-ray energy at a particular scattering angle also may be used to determine properties of the object. For example, the source of a screening system may be modulated between two distinct energies or through a range of more than two energies, and the scatter from the object measured at a particular scattering angle. As discussed below, such a measurement may be used to determine the one or more atomic numbers of the object.

The effective atomic number of a material may be approximated using dual-energy techniques that measure a ratio of photo-electric absorption to Compton scatter along the direction of propagation of the incident x-ray beams (or along the ray). In contrast, a scatter ratio technique, which may use a ratio of Rayleigh scatter to Compton scatter, employs a natively three-dimensional scanning topology that views an object from multiple angles rather than along the ray. In part due to the "along the ray" nature of dual-energy systems, data collected by such systems may show a somewhat significant dependence on external materials, such as a container that holds a material of interest. However, because the scatter-ratio technique is natively three-dimensional, the resulting data has a greatly reduced amount of dependence on external materials. As such, the scatter-ratio technique may produce images and other data that do not include a significant representation of an external container, thus allowing for improved analysis of the contents inside the container.

Further, the scatter-ratio technique may offer improved detection and analysis of organic materials. Scatter is the dominant form of attenuation for an x-ray beam that passes through an organic material, whereas the photo-electric effect is the dominant form of attenuation in a metallic material. Therefore, dual-energy is more sensitive to metallic objects while scatter may be more sensitive to organic objects. While the dual-energy approach produces only a single measure of effective atomic number, scatter is additionally sensitive to each of the multiple atomic numbers of a material composed of multiple elements. Therefore it may be capable of discriminating two materials composed of different elements even when the effective atomic number of each is similar.

At the energy levels typical for a security application, attenuation in organic materials is mostly Compton scatter, except at small scattering angles where Rayleigh scatter is comparable. Excluding the photo-electric effect, attenuation through metals is mostly Rayleigh scatter except at large scattering angles where Compton scatter is comparable. The strength of Rayleigh scatter is approximately proportional to $Z^2$, and the strength of Compton scattering is approximately proportional to Z. In a scatter-ratio based analysis, metals may not dominate over organics because the scatter-ratio measurement is three-dimensional and more than one Z-related term is available (a Z term and a $Z^2$ term). Thus, the scatter-ratio technique may provide improved detection and analysis of organic materials.

Moreover, due to the complementary nature of the dual-energy and scatter-ratio techniques, these two methodologies may be used together to obtain the benefits of both. Additionally, the scatter-ratio technique takes advantage of scattered energy considered to be noise in many x-ray imaging systems. Thus, the scatter-ratio technique may be used to retrofit or further exploit an existing x-ray imaging system to obtain improved performance.

Referring to FIG. 1, an illustration of an example system that determines a material property of an object is shown. The system 100 includes a source 104, a detector 114, and an atomic number determination system 122. The source 104 directs x-ray radiation towards an object 102, and the detector 114 senses x-ray radiation that is scattered by the object 102 and/or radiation that passes directly through the object 102.

The object 102 may be a particle, fluid flow, or a portion of a larger inspection volume 103. For example, the object 102 may be an item in a relatively small volume such as a piece of luggage, or the object 102 may be an item in a relatively large volume such as containerized cargo, container ship, truck, rail car, or another large object used for transportation. In some cases, the object 102 may be positioned within a space, region, object, or a collection of discrete items that does not have a well-defined boundary, such as fluid flow. The object 102 may be made from one or more materials and may include hazardous materials, explosive materials, nuclear materials, or other materials of a particular atomic number or set of atomic numbers.

The object 102 is examined by exposing the object 102 to radiation emanating from the source 104. For example, the source 104 may be a broadband source of x-ray energy and may produce an x-ray beam 106.

Upon interaction with the object 102, the x-ray beam 106 enters the object 102 and may be absorbed. Portions of the x-ray beam 106 that are not absorbed are scattered or pass through the object 102 as a direct beam. In the example shown in FIG. 1, the beam 106 passes into the object 102, is attenuated (or absorbed) by the object 102, and emerges as a direct beam 112 and as scattered signals 108 and 110. The signals 108 and 110 have associated scattering angles, $\theta_1$ and $\theta_2$, respectively. The scattering angle is measured relative to the direct beam 112.

The scatter from the object 102 may be coherent scatter, incoherent scatter, or a combination of both. Coherent scatter (Rayleigh scatter) is characterized by photons of an incident x-ray beam, such as the beam 106, changing direction with no, or very little, loss of energy. The angle of scatter, or scattering angle, of coherent scatter is typically small. For example, the scattering angle associated with most coherent scatter may be about 10° or less or about 20° or less. Incoherent scatter (Compton scatter) is scatter that involves photons of the incident x-ray beam 106 changing direction and losing energy. The scattering angle associated with incoherent scatter is typically larger than the scattering angle of coherent scatter, and incoherent scatter includes backscatter (scatter in a direction that is up to 180° different from the direction of the x-ray beam 106 and the direct beam 112). Equations (1) and (2), discussed below with respect to FIG. 3, show mathematical descriptions of coherent and incoherent scatter, respectively.

Thus, because of the difference between the scattering angles typical of incoherent scatter and those typical of coherent scatter, amounts of incoherent and coherent scatter may be approximated by measuring an amount of scatter as a function of angle relative to the direction of the incident beam.

In the example shown in FIG. 1, the signal 108 is sensed at scattering angles of $\theta_1$ and $\theta_2$. The object 102 also may generate scattered signals at scattering angles other than $\theta_1$ and $\theta_2$. In some cases, scattering angle $\theta_1$ may be associated primarily with coherent scatter and $\theta_2$ may be associated primarily with incoherent scatter.

The detector 114 includes sensor elements 116, 118, and 120, each of which senses radiation coming from the inspection volume 103. In the example shown, the sensor element 116 detects an intensity of the scatter signal 108, the sensor element 118 detects an intensity of the scatter signal 110, and the sensor element 120 detects an intensity of the direct beam 112.

Data collected by the detector 114 is sent to the atomic number determination system 122 to determine a property of the material of the object 102. For example, the effective atomic number of the material of the object 102 may be determined by comparing the intensity of the signal 108 to the intensity of the signal 110. The effective atomic number may also be determined using other methods as described in further detail below.

Figure 2:
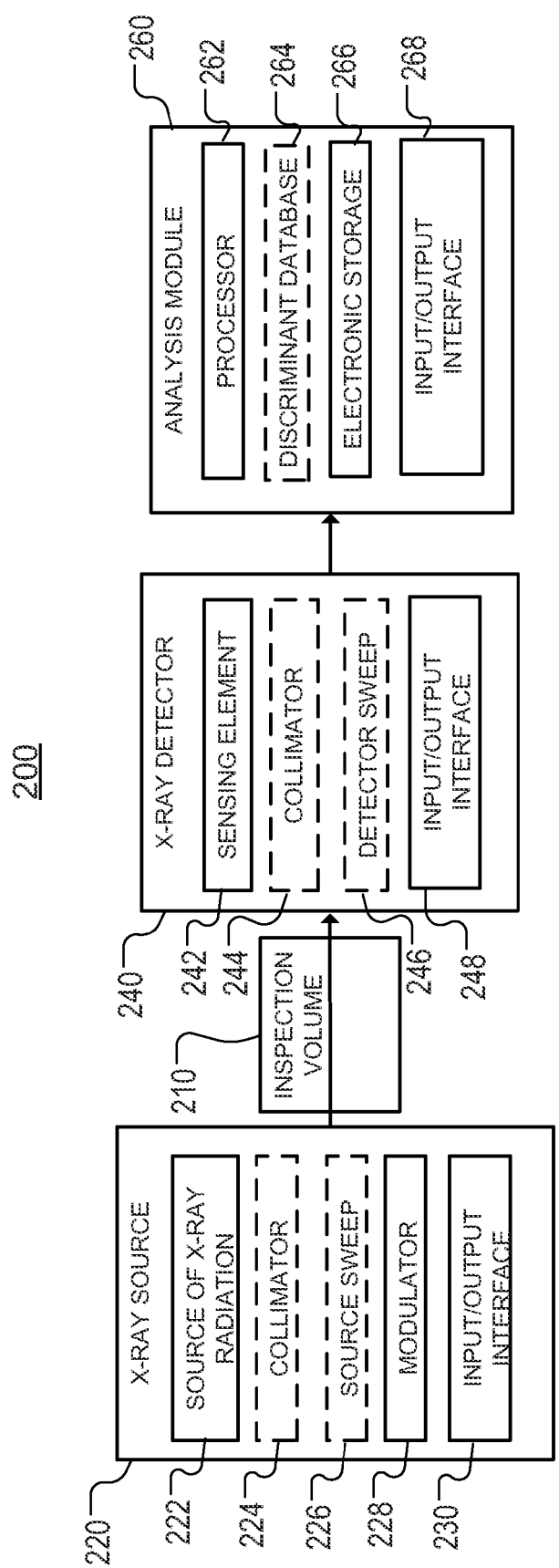
FIG. 2 is a block diagram of an example system that determines a property of a material of an object.

Referring to FIG. 2, a block diagram of an example system 200 is shown. The system 200 includes an x-ray source 220 that exposes an inspection volume 210 to x-ray radiation, an x-ray detector 240 that senses radiation from the inspection volume 210, and an analysis module 260 that receives and analyzes data from the x-ray detector 240 to determine a property of a material in the inspection volume 210. The system 200 may be similar to the system 100 discussed above with respect to FIG. 1.

The inspection volume 210 may be similar to the inspection volume 103 discussed above with respect to FIG. 1. The inspection volume 210 may include one or more objects. The inspection volume 210 may be a volume that is partially or completely enclosed by a defined structure. For example, the inspection volume 210 may be a luggage case, a shipping container, a bottle, a pipe, or a portion of an objection inspection system. In some examples, the inspection volume 210 may be an arbitrarily defined region within or surrounding an object of interest, such as the object 102.

The x-ray source 220 exposes the inspection volume 210 to x-ray radiation and includes a source of x-ray radiation 222, a collimator 224, a source sweep 226, a modulator 228, and an input/output interface 230. The x-ray energy produced by the source 222 may be between 10 peak kilovoltage (kVp) and 200 kVp, between 200 kVp and 500 kVp, or greater than 500 kVp. In some implementations, the x-ray energy produced by the source 220 may be as much as 20 MVp. The x-ray energy from the source 222 may be modulated among these various energies by the modulator 228. In some implementations, the modulator 228 may be implemented as a filter placed over the source 222. The collimator 224 may be used to collimate a beam from the source 220. The collimator 224 may be made of lead with a slit or opening for x-rays to pass, and the collimator 224 may be a filter wheel. The collimator 224 may be made of any material that is impenetrable to x-rays. In implementations that include a movable source, the source sweep 226 may provide for or cause the motion of the source.

The input/output interface 230 may include any device able to transmit data to, and receive data from, the x-ray source 220. For example, the input/output interface 230 may be a mouse, a touch screen, a stylus, a keyboard, or any other device that enables a user to interact with the x-ray source 220. In some implementations, the input/output interface 230 may be configured to receive an input from an automated process or a machine or to provide an output to an automated process or a machine.

The x-ray detector 240 senses the radiation energy from the inspection volume 210. The x-ray detector 240 includes a sensing element 242, a collimator 244, a detector sweep 246, and an input/output interface 248. The sensing element 242 senses radiation from the x-ray source 220 and may indicate a position and/or an intensity of the sensed radiation energy. The collimator 244 and the detector sweep 246 may be optional elements of the x-ray detector 240 that may provide additional functionalities as discussed further below.

The input/output interface 248 may be any device able to transmit data to, and receive data from, the x-ray detector 240. For example, the input/output interface 248 may be a mouse, a touch screen, a stylus, a keyboard, or any other device that enables a user to interact with the x-ray detector 240 and/or to retrieve data from the x-ray detector 240. In some implementations, the input/output interface 248 may be configured to receive an input from an automated process or a machine or to provide an output to an automated process or a machine. Additionally, the input/output interface 248 passes data and/or signals generated by the sensing element 242 to the analysis module 260. The data and/or signals from the sensing element 242 may be, for example, electrical or optical signals.

The sensing element 242 may be any sensor that measures x-ray fluency, measures the x-ray fluency and the per-photon energy deposited on the sensor, or the total x-ray energy deposited. The sensing element 242 may be, for example, a solid-state detector, such as a germanium (Ge) detector or a cadmium zinc telluride (CZT) detector, a photo-multiplier tube or photodiode with scintillating materials, or a Geiger counter.

The analysis module 260 receives and analyzes data from the x-ray detector 240 to determine a property of a material in the inspection volume 210. The analysis module 260 includes an electronic processor 262, a discriminant database 264, an electronic storage 266, and an input/output interface 268. The analysis module 260 may be co-located with the x-ray detector. However, this is not necessarily the case, and the analysis module 260 may be located remotely from the other components of the system 200 while being in communication with the other components of the system 200. Data from the x-ray detector 240 may be analyzed in real-time, or near real-time, as it is received from the x-ray detector, or the data may be stored for later analysis.

The processor 262 may be a processor suitable for the execution of a computer program such as a general or special purpose microprocessor, and any one or more processors of any kind of digital computer. Generally, a processor receives instructions and data from a read-only memory or a random access memory or both. The processor 262 receives data from the components of the x-ray detector 240 and uses the data to, for example, compute an atomic number of a material detected within the inspection volume 210. In some implementations, the analysis module 260 includes more than one processor.

The analysis module 260 may include the discriminant database 264. The discriminant database 264 includes pre-computed data that shows scattering characteristics of known materials. For example, the discriminate database 264 may include data that expresses the theoretically expected coherent scatter and/or incoherent scatter as a function of scattering angle for a known material at multiple different energy levels of an x-ray source. The processor 262 may use the data and values stored in the discriminant database 264 to compare and analyze the data received from the x-ray detector 240.

The electronic storage 266 stores instructions that, when executed by the processor 262, allows the analysis module 260 to, for example, determine an effective atomic number of an object within the inspection volume 210. The storage 266 also may store data sensed by the x-ray detector 240, instructions for retrieving the data from the x-ray detector 240, and instructions for comparing the data from the x-ray detector 240 to the discriminant database 264. The storage 266 is an electronic memory module, and the storage 266 may be a non-volatile or persistent memory. The storage 266 may be volatile memory, such as RAM. In some implementations, the storage 266 may include both non-volatile and volatile portions or components.

The input/output interface 268 may be any device able to transmit data to, and receive data from, the analysis module 260. For example, the input/output interface 268 may be a mouse, a touch screen, a stylus, a keyboard, or any other device that enables a user to interact with the analysis module 260. In some implementations, the input/output interface 268 may be configured to receive an input from an automated process or a machine or to provide an output to an automated process or a machine. The input/output interface 268 also receives data and signals from the x-ray detector 240.

Figure 3A:
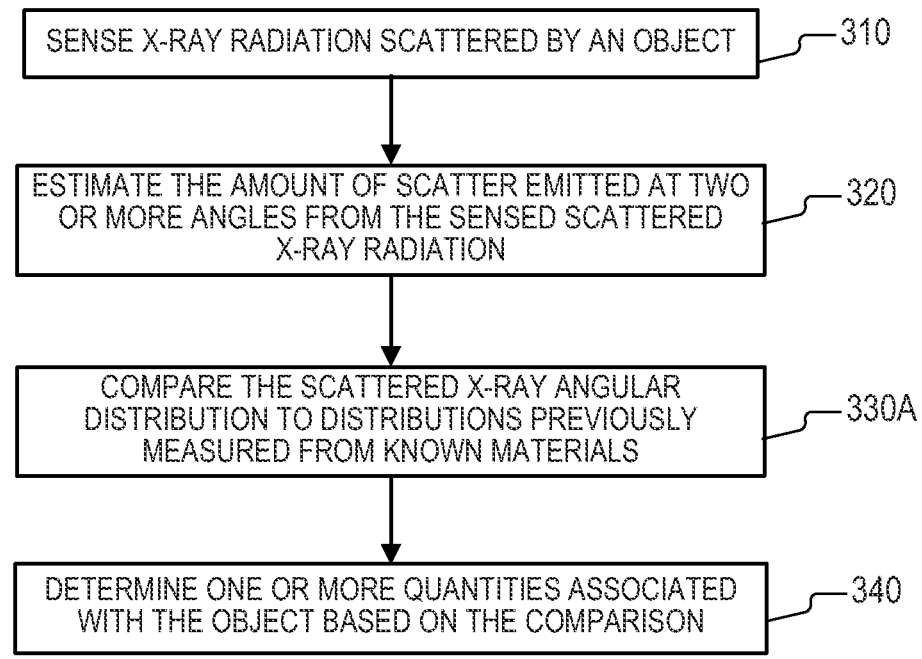
FIGS. 3A and 3B are flow charts of example processes for determining a property of a material.
Figure 3B:
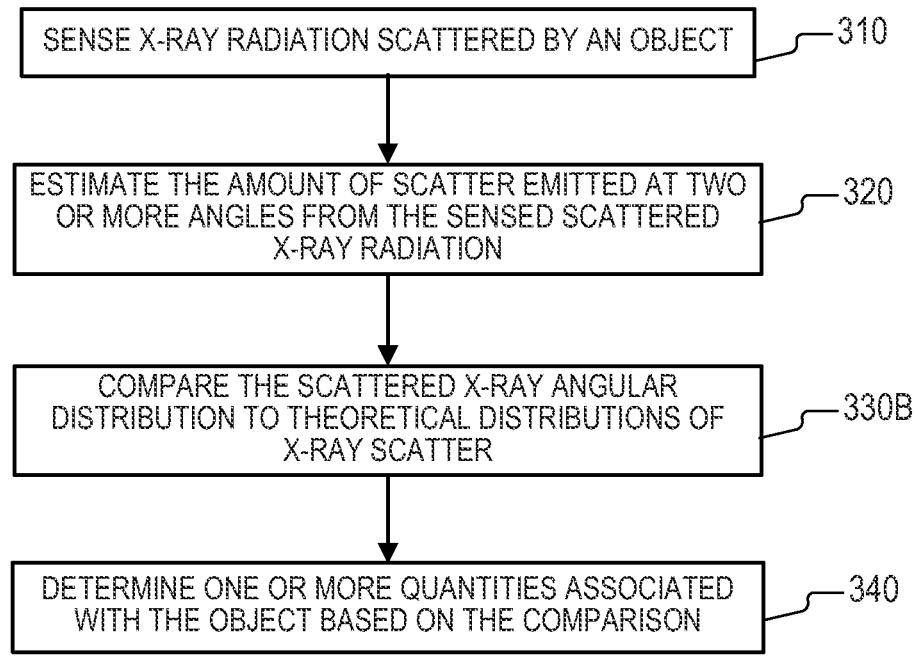

Referring to FIGS. 3A and 3B, example processes 300A and 300B, respectively, for determining a material property of an object are shown. The example process 300A compares the amount of scatter sensed to x-ray angular distributions previously measured from known materials to determine a quantity associated with the object. The example process 300B compares the amount of scatter sensed to theoretical distributions of x-ray scatter. The example processes 300A, B may be performed by one or more processors such as the processor 262 in the analysis module 260 discussed above, or the atomic number determination system 122. Although the example processes 300A, B are described using x-ray radiation, other forms of electromagnetic radiation, such as gamma radiation, may be used.

X-ray radiation scattered by an object is sensed (310). The sensed x-ray radiation may be referred to as observed scatter data. The object, such as the object 102 discussed above, may be interrogated by x-ray radiation produced by one or more sources. For example, the x-ray source 220 of the example system 200 may be used to direct an x-ray beam towards the object. The scattered x-ray radiation may be sensed by one or more detectors such as the x-ray detector 240 or the detector 114. The scattered x-ray radiation may include data measured at two distinct energies at a particular scattering angle.

From the sensed scattered x-ray radiation data, amounts of scatter produced at one or more angles are determined (320). Scatter from an object may be described in terms of contributions from relative coherent and incoherent scattering cross-sections. The scattering cross section represents a probability of generating scatter in a particular direction. An expression for the relative coherent scattering cross section for a single element is shown below in Equation (1), and an expression for the relative incoherent scattering cross section for a single element is shown in Equation (2):

$$\frac{d\sigma_{coherent}}{d\theta} = \pi r_e^2 \sin\theta \cdot (1 + \cos^2\theta) \cdot F(x, Z)^2 \quad (1)$$

$$\frac{d\sigma_{incoherent}}{d\theta} =$$
$$\pi r_e^2 \sin\theta \left[1 + k(1 - \cos\theta)\right]^{-2} \cdot \left[1 + \cos^2\theta + \frac{k^2(1-\cos\theta)^2}{1+k(1-\cos\theta)}\right] \cdot S(x, Z) \quad (2)$$

where $$k = \frac{E}{511 \text{ keV}},$$

$$x = \sin\frac{\theta}{2} \cdot \frac{E}{12.39852 \text{ keV}} \left[\frac{1}{\text{Å}}\right], \text{ and}$$

$$r_e^2 = 7.94 \times 10^{-30} \text{ m}^2.$$

F(x,Z) and S(x,Z) may be referred to as the scattering factors, with F(x,Z) also being referred to as the atomic form factor, and S(x,Z) also being referred to as the incoherent scattering factor. In the limit of small x (small scattering angle), F(x,Z) is approximately equal to the effective atomic number ($Z_{eff}$) of the material, and S(x,Z) is approximately 0. For large x (large scattering angle), S(x,Z) is approximately equal to Z and F(x,Z)=0. Thus, for a given scattering angle (A), and a given x-ray energy (k or E), the cross section of coherent and incoherent scatter is dependent only on, or is substantially dependent on, the atomic number of the object. For objects composed of multiple elements, the scatter cross sections are a sum of the terms from the individual elements weighted by their concentration within the object. As such, the observed scatter at a particular scattering angle and x-ray energy may be used to estimate the atomic number (Z), which in turn leads to identification of the material as a particular material.

Figure 5A:
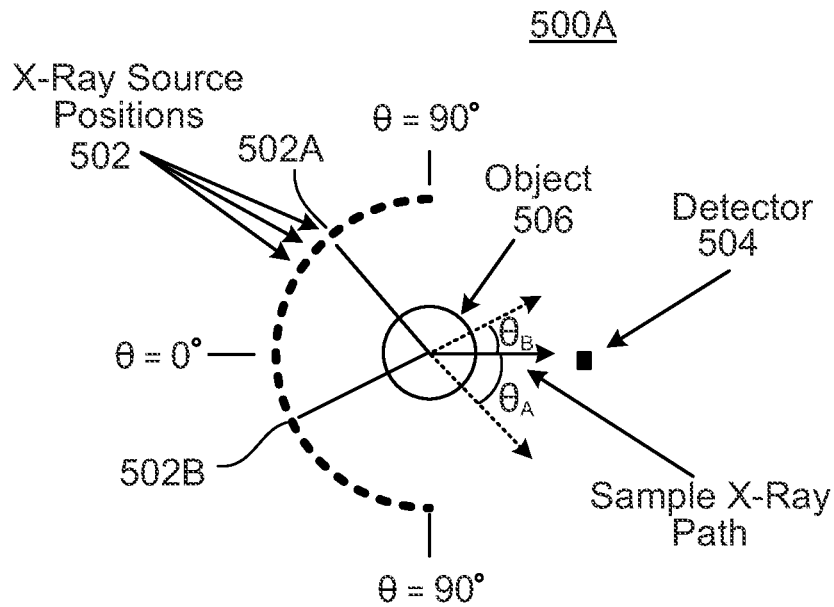
FIG. 5A is an example of a system that includes radiation sources.
Figure 5B:
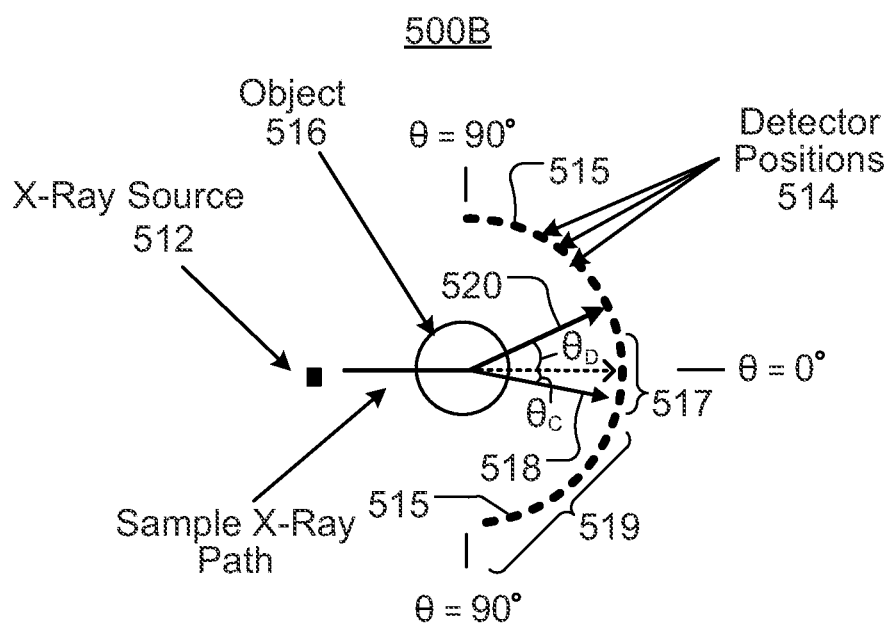
FIG. 5B is an example of a system that includes detectors.
Figure 5C:
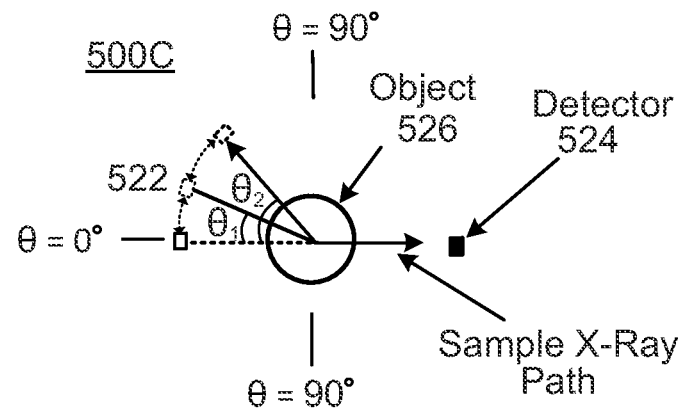
FIG. 5C is an example of a system that includes a moving radiation source.
Figure 5D:
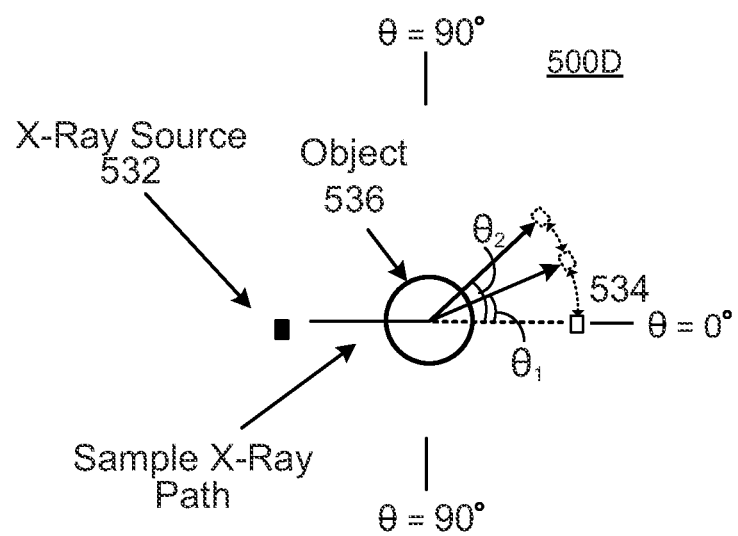
FIG. 5D is an example of a system that includes a moving detector.

As discussed above, the atomic number may be estimated from data generated from irradiating an object with a known x-ray energy and measuring an amount of scatter generated by an object at two distinct angles. One angle may be associated with coherent scatter and the other angle may be associated with incoherent scatter. In some implementations, additional observed scatter data may be generated by measuring the scattered radiation at additional, distinct angles relative to the direction of the beam of incident x-ray radiation. For example, measurements at ten or thirty different angles may be made. At each angle, the contribution of coherent and incoherent scatter to the total amount of scattered radiation can be determined by the above expressions. Referring briefly to FIG. 5A, the additional measurements may be made by positioning multiple sources around the object, or, as shown in FIG. 5B, by positioning multiple fixed detectors around the object. In some implementations, as shown in FIG. 5C, a single source may move relative to the detector, or, as shown in FIG. 5D, a single detector may move relative to the source to collect data at different scattering angles. Additionally, by measuring scatter at multiple angles, a scattering cross-section vs. scattering angle distribution may be obtained.

Alternatively, and referring again to Equations (1) and (2), the amounts of coherent and incoherent scatter may be estimated by measuring the amount of total scatter at any one angle while varying the x-ray energy that is output by the source that irradiates the object 102 through at least two energies. For example, the source 220 may be modulated to vary its energy by having more than one x-ray source, running a particular x-ray source at multiple energies, or having different material filters over the x-ray source at different times. The x-ray energy may be modulated by using the modulator 228.

In other examples, measurements of incoherent and coherent scatter are generated from a measurement of one or more small angle diffraction spectra, and the coherent scatter is estimated from the diffraction peaks. The incoherent scatter may be estimated as the background to the diffraction peaks or from the total observed attenuation. In other examples, inspection of different regions of a suitably homogeneous object (such as a liquid or a plastic slab) may each provide a measurement of a different scattering angle. In other words, in the case of a homogeneous material, inspection of one region may provide a measure of coherent scatter, and inspection of another region of the object may provide a measure of incoherent scatter. In such cases, one or more sources 220 may inspect different regions of the object, generating scatter that is sensed by one or more x-ray detectors 240. In this case, the amount of scatter generated from one region of the object is compared with the amount of scatter generated from one or more other regions of the object, where each region of the object sensitive to a different scattering angle. FIG. 7C, discussed below, illustrates an example of a system for inspecting a homogeneous material.

As such, there are multiple techniques for determining, measuring, or otherwise ascertaining an amount of coherent scatter and an amount of coherent scatter. The process 300 may employ one or more of the techniques, and the techniques may be used in combination with each other.

The amount of scatter produced at different angles is evaluated (330A/330B). The processor 262 of the analysis module 260, for example, may be used to evaluate the scatter by comparing the scattered x-ray angular distribution to distributions previously measured from known materials (330A) or by comparing the scattered x-ray angular distribution to theoretical distributions of x-ray scatter (330B). Evaluating the scatter may include determining a ratio of the amount of scatter produced at two different angles.

A quantity associated with the object of interest is determined based on the evaluation of scatter (340). For example, the quantity may be an atomic number (Z) of a material of the object 102. In some cases, to determine the Z, the ratio of the scatter at two or more angles may be compared to a pre-existing database or table that includes the ratio of scatter for known types of materials. In some implementations, one or more atomic numbers of the object may be determined from direct calculations using Equations (1) and/or (2) and the knowledge of the scattering angle (A) and the x-ray energy (E). The scattering angle can be known from the location of the detector relative to the object 102 and the detector 114, and the x-ray energy can be known from the source 104.

Figure 4A:
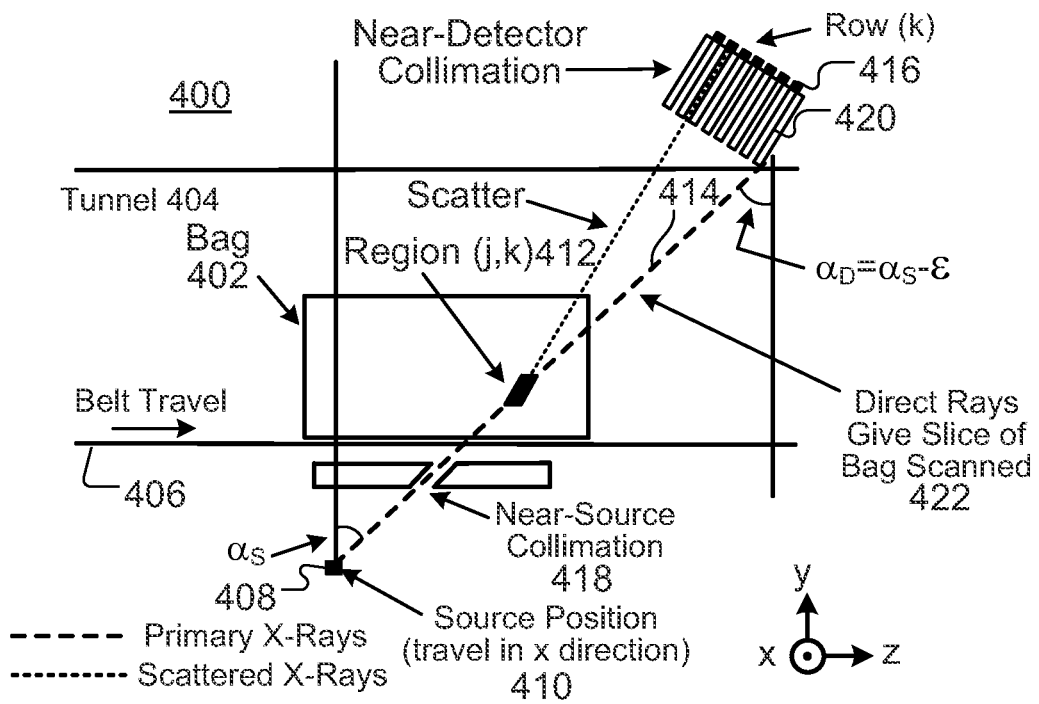
FIG. 4A is a longitudinal view of an example system that determines a property of a material.
Figure 4B:
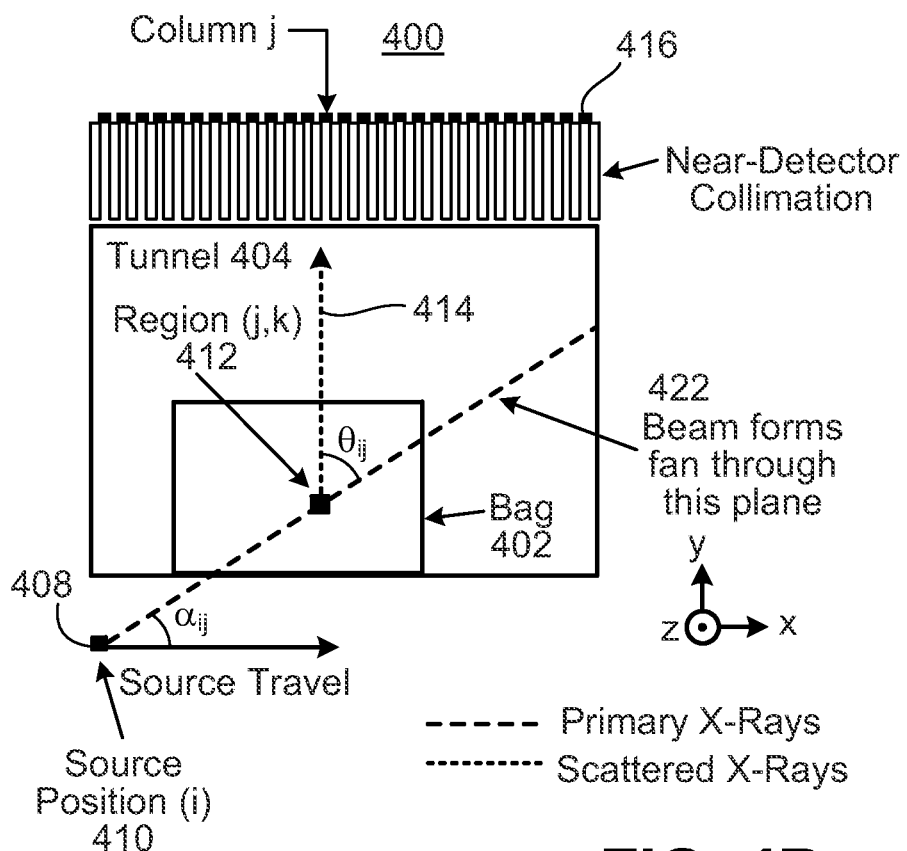
FIG. 4B is a transverse view of the system shown in FIG. 4A.

Referring to FIGS. 4A and 4B, an example system 400 illustrates one implementation of a system for determining a material property using scattered radiation. FIG. 4A shows a longitudinal view of the system 400, and FIG. 4B shows a transverse view of the system 400. A property of a material of the bag 402 and/or the contents of the bag 402 may be determined using scattered radiation.

FIG. 4A shows a longitudinal view of the system 400. The system includes a tunnel 404, a belt 406, an x-ray source 408, a detector 416, a near source collimator 418, and a collimator 420. The bag 402 is positioned on the belt 406 and travels in the "z" direction through the tunnel 404. The x-ray source 408 is positioned at a source position 410, which moves in the "x" direction and directs x-ray radiation towards a region 412 of the bag 402. Following interaction with the x-ray radiation, the region 412 generates direct x-rays 422 and scattered x-rays 414. The scattered x-rays 414 are detected by the detectors 416. The detectors 416 may be arranged in a two-dimensional array pattern, with each detector in the array identified, for example, by row (k) and column (j). The detectors 416 may be positioned anywhere within or outside of the tunnel 404, for example along a top surface of the tunnel 404 and across from the source position 410, such that the scattered x-rays 414 may be detected.

A near-source collimator 418 is positioned between the source 408 and the region 412. The near-source collimator 418 creates a narrow x-ray plane that passes into the tunnel 404 and the bag 402. The near-source collimator 418 may be a slit between two pieces of material that are impenetrable to x-rays. The system 400 also includes the collimators 420. In some cases, the collimators 420 may be a translated opening, such as a slit. In some cases, the collimators 420 may be a filter wheel.

The collimators 420 are positioned between the region 412 and the detectors 416, and the collimators 420 allow the detectors 416 to select x-rays on a line through the x-ray plane created by the near-source collimator 418. The collimators 420 prevent, or greatly reduce, the direct x-rays 422 from reaching the detectors 416. As such, the collimators 420 allow only the scattered x-rays 414 to be sensed by the detectors 416. In this manner, the scattered x-rays 414, which are generally weaker in intensity than the direct x-ray 422, are detected without being dominated by the direct x-rays 422. This allows the scattered x-rays 414 to be utilized for material characterization. In use, each row (k) of the array of detectors 416 selects a different line of the scattered x-rays 414, allowing a full height of the bag 402 to be probed.

Referring also to the transverse perspective shown in FIG. 4B, a full width of the bag 402 within the tunnel 404 may be probed by using different columns of the array of detectors 416. The source 408 at the source position 410 generates a fan beam that may span the width of the tunnel 404. Thus, each column (j) of the array of detectors 416 selects a different x-position in the tunnel 404. By combining data gathered from the row (k) and column (j) of the detectors 416 with a time (t) derived from the movement of the bag 402 within the tunnel 404, the detectors 416 may uniquely define a full three-dimensional (3-D) region within the tunnel 404. In FIG. 4B, a scattering angle $\theta_{ij}$ depends on a fixation angle of the collimators 420, variations in the source position 410, and the column (j) of the detectors 416. This information may in turn provide an observed scatter distribution as a function of scattering angle that may be used to determine the atomic number of the region 412 using, for example, the example process 300.

Each of FIGS. 5A-5D shows an example of a system for measuring scatter from an object as a function of angle. The data collected by such a system may be referred to as observed angular scatter data. As discussed below, by including multiple sources and/or multiple detectors positioned at various locations around an object, the amount of scatter from an object may be measured as a function of scattering angle. In each of the systems shown in FIGS. 5A-5D, the direct x-rays are prevented from reaching the detectors of the system.

Referring to FIG. 5A, an example system 500A includes multiple sources of radiation. The system 500A includes multiple sources of radiation located at source positions 502, including positions 502A and 502B, and a detector 504. Each of the multiple sources of radiation produces a beam of radiation that is directed towards the object 506. The object 506 scatters the radiation at various angles, such as the angles $\theta_A$ and $\theta_B$, which are measured by the detector 504 relative to the direction of the incident beam.

As discussed above, to determine the atomic number (Z) at a single energy level, the amount of scatter is measured at multiple scattering angles. In the system 500A, the scattering angle is varied based on the position or positions of the activated sources. For example, when the source in position 502A is activated, the detector 504 measures scattering at the scattering angle $\theta_A$. When the source in position 502B is activated, the detector 504 measures scattering that occurs at the scattering angle $\theta_B$.

Although in the example of FIG. 5A, the sources are shown in a semi-circle, the sources may be arranged in any other manner about the object. For example, the sources may be arranged in a linear array. In some instances, arranging the sources in a linear array may result in cost savings due to relatively simpler alignment and manufacturing.

FIG. 5B shows a system 500B that includes an x-ray source 512, an object 516, and detectors 515 in multiple positions 514. When the x-ray source 512 irradiates the object 516, the object 516 scatters x-ray radiation at various angles, including $\theta_C$ and $\theta_D$. As such, radiation at multiple scattering angles is detected with detectors 515. The detectors 515 in the detector positions 514 may be used to, for example, retrofit an existing screening system that includes a single detector into a system that determines material properties using scattered x-rays.

Although the example shown in FIG. 5B includes twenty-four detectors 515, any suitable number of detectors may be used. In other examples, two detectors, ten to thirty, more than thirty, or more than 100, for example, may be used. Additionally, the example shown is a configuration in which the detectors are arranged about the object in a semi-circular configuration. However, other arrangements may be used. For example, the detectors may be positioned along a linear path.

Referring to FIG. 5C, a system 500C includes a moveable source 522 and a stationary detector 524. The source 522 moves relative to an object 526 such that the radiation that the detector 524 senses is attributable various scattering angles. FIG. 5D shows a system 500D that includes a stationary source 532 and a movable detector 534. The detector 534 moves relative to an object 536 such that the detector 534 senses radiation scattered at different scattering angles as the detector 534 moves relative to the object 536. In FIG. 5C, the source 522 is shown as moving along an arc, and, in FIG. 5D, the detector 534 moves along an arc. However, either or both of the source 522 and the detector 534 may move in another manner relative to the object 526. For example, the source 522 and/or the detector 534 may move along a linear path.

In addition to the examples shown in FIGS. 5A-5D, a system may include multiple sources and multiple detectors, or a system may include a moving source and a moving detector.

Figure 6:
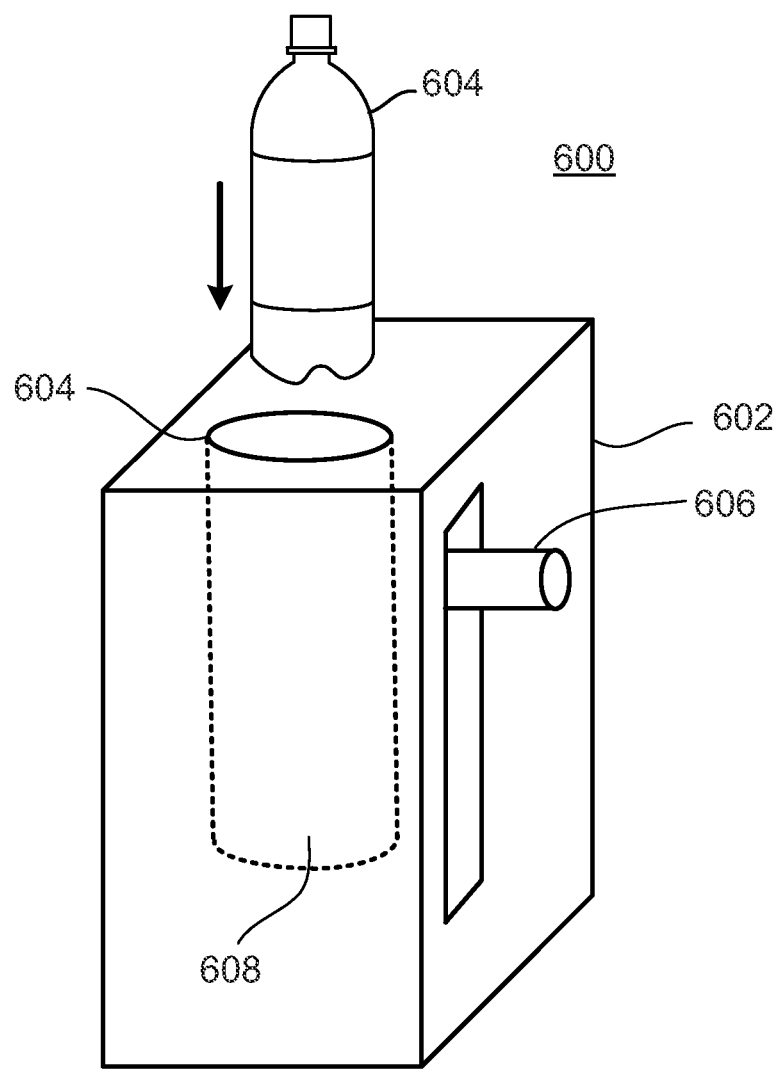
FIGS. 6 and 7A-7C are illustrations of example systems for determining a property of a material.

Referring to FIG. 6, another example screening system is shown. The system 600 includes a housing 602, an opening 604, and a slider 606. In the example shown, the opening 604 is shaped to receive a bottle 607, and the opening 604 leads to a receptacle 608 that holds the bottle 607 during screening. The slider 606 is used to position the bottle 607 in the receptacle 608. In other examples, the opening 604 is sized to receive other hand-carried items, such as packaged foodstuffs or handbags, that contain objects and or materials.

In some implementations, the system 600 may include an x-ray source (not shown) in the housing 602, and an array of detectors. The array of detectors may include, for example 100 channels or less. The system 600 also may include optical sensors (not shown) to estimate the outer dimensions of the bottle 607 and/or the system 600 may determine a total amount of x-ray attenuation caused by the bottle 607 and its contents by transmitting an x-ray beam through the bottle 607 and measuring an intensity of the resulting direct beam (the beam that travels along the same direction as the beam that is incident on the bottle 607).

In use, the system 600 measures the effective atomic number of the interior contents of the bottle 607 (independent of the material of the bottle 607) using scattered x-ray radiation as discussed above with respect to FIG. 3.

Figure 7A:
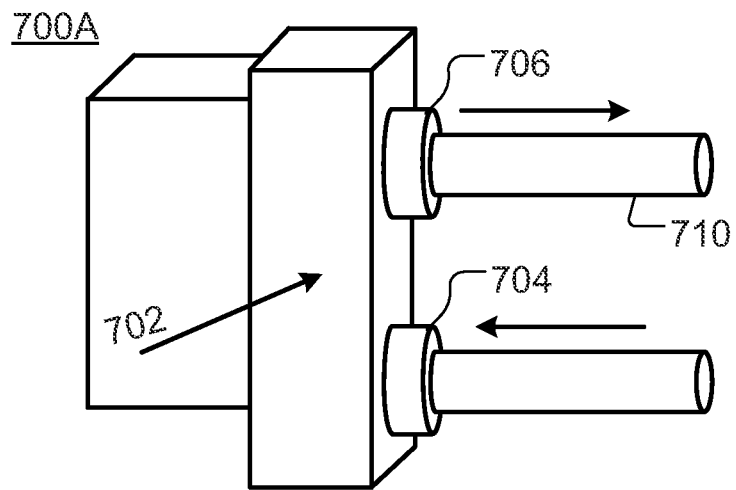
Figure 7B:
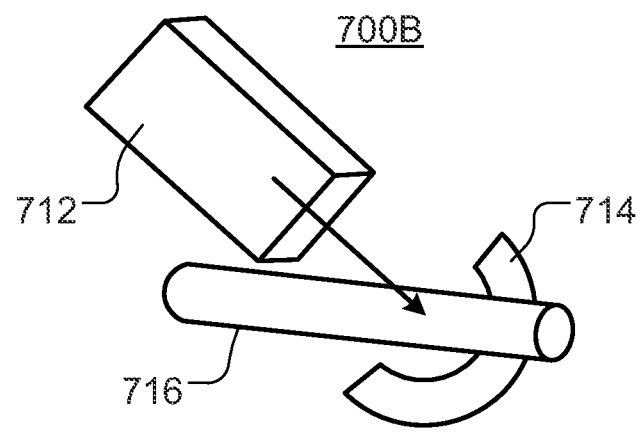
Figure 7C:
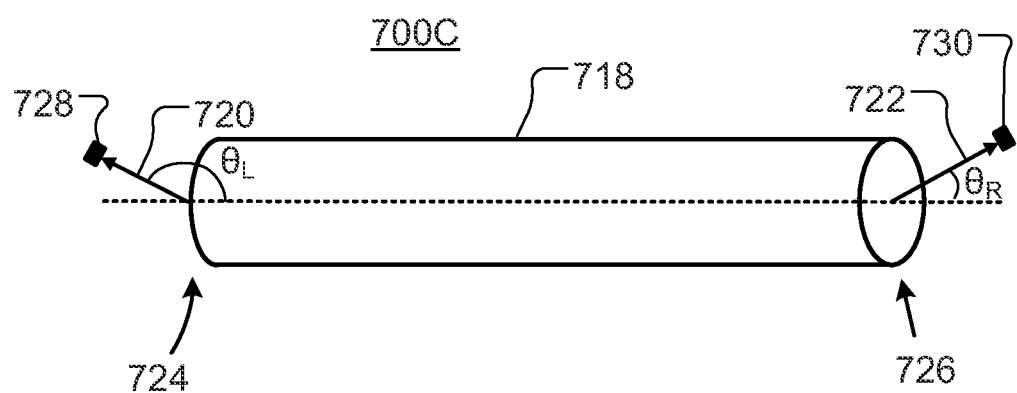

FIGS. 7A-7C show examples of systems that may be used for non-destructive testing. The system 700A of FIG. 7A may be used for continuous testing of a flowing material, and the system 700B of FIG. 7B may be removably attached to a pipeline or other container of flowing material to test a material in the container. Both the systems 700A and 700B allow determination of a property of a material without removing the material from its container. FIG. 7C shows an example system that may be used for testing a homogeneous material.

Referring to FIG. 7A, the system 700A includes a radiation unit 702, an inlet 704, and an outlet 706. The system 700A is built into a portion of a monitored process or system. For example, the inlet 704 and the outlet 706 may be directly and/or permanently connected to a pipeline that carries a flowing fluid through the monitored process. The system 700A may be referred to as in-line or integrated with the process monitored by the system 700A. In the example shown in FIG. 7A, the inlet 704 is in fluid communication with a pipeline bypass 708 that draws fluid from the monitored process, and the outlet 706 is in fluid communication with a pipeline bypass 710 that returns the fluid to the monitored process.

In this configuration, the inlet 704 receives fluid that is flowing in the monitored process, passes the fluid through the radiation unit 702, and returns the fluid to the monitored process through the outlet 706. Thus, the system 700A provides continuous and non-destructive monitoring of the processes, and an amount of fluid in the monitored process is not reduced by testing the fluid with the radiation unit 702. The radiation unit includes one or more sources of x-ray radiation (not shown) and one or more detectors (not shown). The source(s) irradiate the fluid of the process, and the detectors sense x-ray radiation scattered from the fluid. Properties of the fluid, such as density variations and effective atomic number ($Z_{eff}$) may be determined based on the scattered x-rays.

Referring to FIG. 7B, the system 700B also provides non-destructive testing and monitoring of a process. The system 700B includes a radiation unit 712 and an attachment piece 714. The radiation unit includes one or more x-ray sources (not shown) and one or more detectors (not shown). The system 700B may be removably attached to or around a pipeline 716 or other container of fluid of the monitored process. For example, the radiation unit 712 may be clamped on to the pipeline 716 by attaching the radiation unit 712 to the attachment piece 714 such that the pipeline 716 is placed between the radiation unit 712 and the attachment piece 714.

In this configuration, the sources in the radiation unit 712 penetrate the pipeline 716 and pass into the fluid in the pipeline 716. Scattered x-rays from the fluid are detected by the detectors and used to determine properties of the fluid, such as effective atomic number and density.

FIG. 7C shows another example system for non-destructive testing. The system 700C includes two detectors 728 and 730, each placed on an end of a uniform object 718.

In the example shown in FIG. 7C, scatter 720, 722 is generated, respectively, at two ends 724, 726 of a homogeneous object 718 when a beam passes through the object in a direction 719. Because the object 718 is known to be, or is expected to be, homogeneous, the atomic number of the object 718 is the same at the end 724 as it is at the end 726. The portion of the object 718 that is between the ends 724 and 726 is also homogeneous and the atomic number is constant, or approximately constant, throughout the object 718. Because the object 718 is homogenous, coherent and incoherent scattering from the object 718 may be measured at different angles by measuring scattering from different ends (or sides) of the object 718 and without using a detector array. As a result, the system 700C is a relatively compact system.

The object 718 may be a pipe filled with a liquid of a uniform density. In other examples, the object 718 may be a slab of a homogeneous plastic that has a uniform density throughout the slab. Scatter 720 has a scattering angle of $\theta_L$ and is detected by a single detector 728 positioned near the end 724. Similarly, scatter 722 has a scattering angle of $\theta_R$ and is detected by a single detector 730 positioned near the end 726. Because the object 718 is homogeneous, the scattering measurements may be one scattering measurement at each end of the object 718 instead of multiple scattering measurements taken by detectors oriented at multiple angles with respect to the object 718 at a single end of the object 718. In other words, for a homogeneous object, scattering measurements taken at different angles on opposite sides of the object may produce the same, or very similar, results as scattering measurements taken at different angles on the same side of the object.

FIGS. 8A-8C, 10A-10G, 11, and 12 show additional example processes that may be used to determine a property of a material or may be used as part of such a process. Each of the example processes shown FIGS. 8A-8C, 10A-10G, 11, and 12 may be performed by one or more processors such as the processor 262 in the analysis module 260 discussed above, or the atomic number determination system 122. For example, an example process 800 (FIG. 8A) may be performed on data collected from a system such as the system 100 or from an x-ray diffraction system.

Figure 8A:
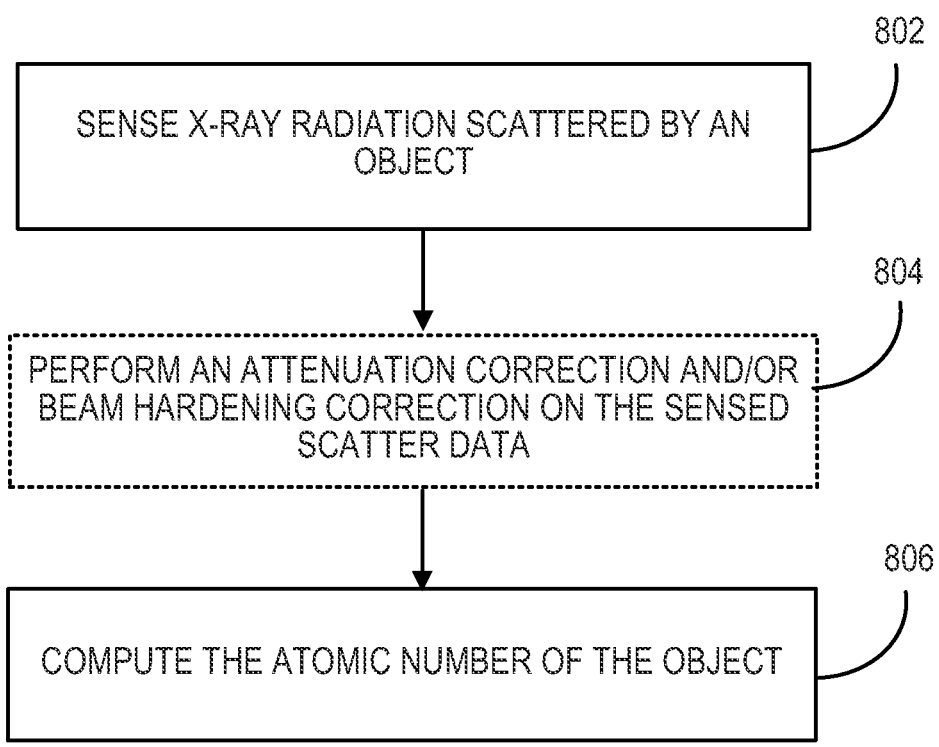
FIGS. 8A-8C are flow charts of example processes for computing an atomic number of an object.

Referring to FIG. 8A, the example process 800 for determining an atomic number of an object is shown. X-ray radiation scattered by an object is sensed (802). The sensed x-ray radiation may be referred to as observed scatter data. The object may be an object such as the object 102. The x-ray radiation sensed may be scattered x-ray flux measured at two or more scattering angles. In this instance, the x-ray radiation may be referred to as an observed angular scatter distribution or as observed angular scatter data. The observed angular scatter distribution includes an intensity, flux, or other measure of scattered radiation as a function of scattering angle. The scattering angle may be varied by, for example, moving the source(s) (FIG. 5C) or moving the detector(s) (FIG. 5D).

In other examples, the x-ray energy may be varied and the scatter measured at a particular scattering angle for each different energy. The sensed x-ray radiation in this instance may be referred to as observed energy dependent scatter.

In some implementations, the observed scatter data is corrected with an attenuation correction and/or a beam hardening correction (804).

Figure 9:
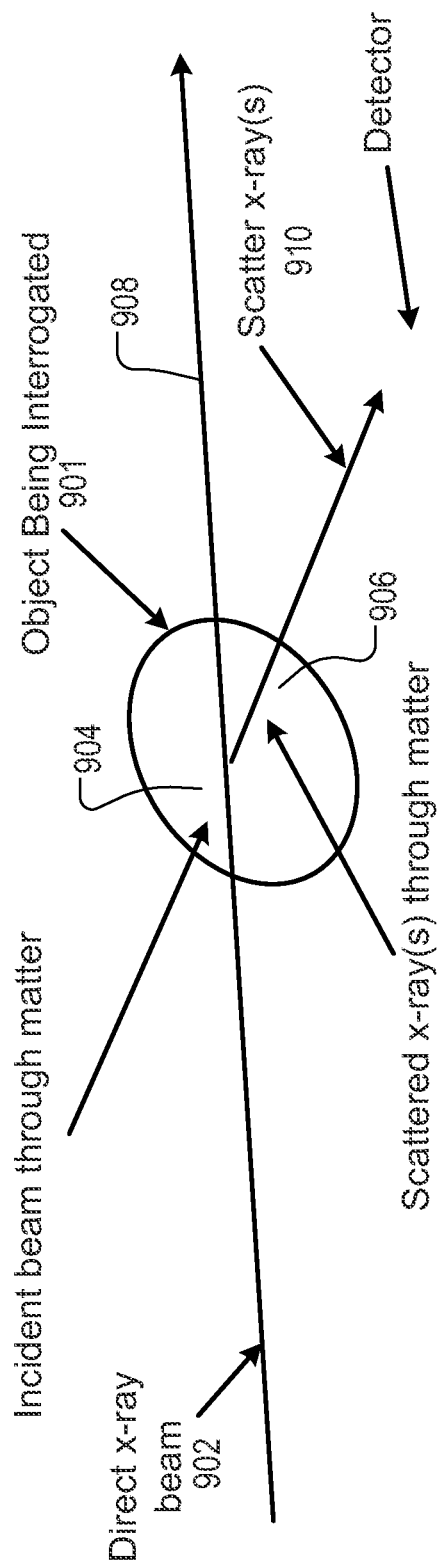
FIG. 9 illustrates scattering and attenuation by an object interrogated by an x-ray beam.

With respect to the attenuation correction, in applications in which the object 102 is relatively large (such as a suitcase or cargo container), the object 102 attenuates the x-rays that are incident upon it in addition to generating scatter. FIG. 9 shows an illustration of scattering and attenuation by an object interrogated by an x-ray beam. In the example shown in FIG. 9, an incident x-ray beam 902 interrogates an object 901. The beam 902 enters the object 901 and is absorbed and scattered into an attenuated beam 908, and scattered x-rays 910. An attenuation correction may be applied to compensate for the effects of attenuation caused by the incident beam 902 passing through portions 904 and 906 of an object 901. For example, the x-ray attenuation through the portions 904 and 906 may be estimated according to Equation (3):

$$I=I_o e^{-\mu d} \quad (3)$$

In Equation (3), I° is the intensity of the incident beam 902, I is the measured intensity of the direct beam 908, μ is a material-specific attenuation parameter, and d is the thickness of the object 901. Due to the attenuation caused by the object 901, the intensity of the attenuated beam 908 and the scattered x-rays 910 may be less than expected. This reduction may be accounted for by inverting Equation (3) to restore $I_0$, from I, the measured intensity of the attenuated beam 908, the attenuation parameter (μ), and the thickness (d) of the object 901. The thickness (d) of the object 901 is not known, but may be obtained from a volumetric computed tomography (CT) image. Thus, the intensity of the scattering x-rays may be corrected for attenuation caused by the object 901.

With respect to the beam hardening correction, beam hardening may occur when objects, such as steel and other metals, are in the path of direct or scattered x-ray beams. The presence of such steel or other objects may cause the average energy of the incident x-ray beam 902 to change because the object absorbs relatively more low energy x-rays than high energy x-rays. Because equations for scatter, such as Equations (1) and (2) depend on x-ray energy (E), the change in energy due the presence of extraneous objects may skew the determination of a property of the material. Thus, including the beam hardening correction may result in a more accurate estimate of the property or figure of merit related to the property.

An atomic number of a material in the object 102 is computed (806). As shown in Equations (1) and (2), the incoherent and coherent cross-sections are functions of scattering angle (A), x-ray energy (E), and atomic number (Z). Therefore, the atomic number of the material may be computed from the measured amounts of incoherent and coherent scattered radiation. In implementations in which a larger object is screened, the effects of attenuation may be accounted for prior to computing the atomic number.

Figure 8B:
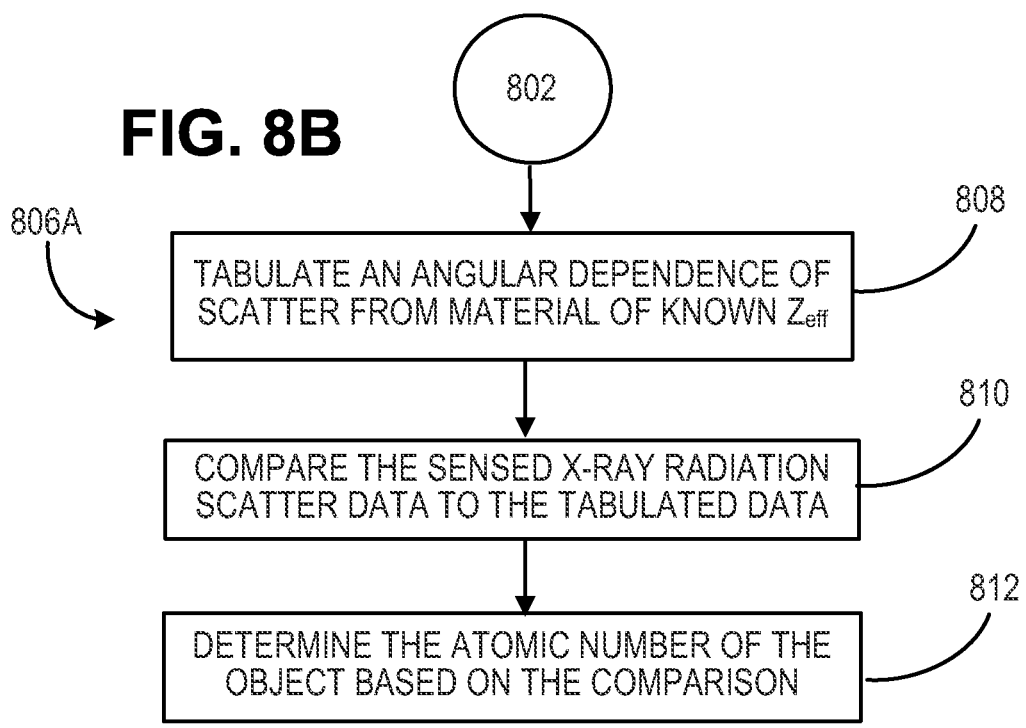
Figure 8C:
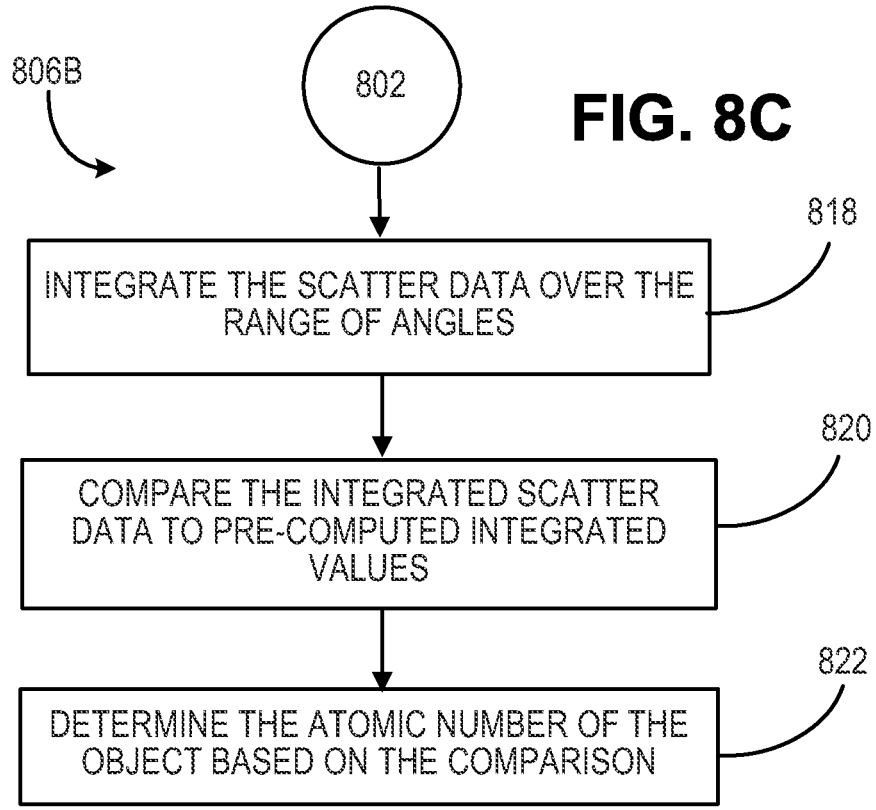

FIGS. 8B and 8C show example processes for computing the atomic number (806). Referring to FIG. 8B, example process 806A may be used as (806) in the example process 800. In example process 806A, the observed angular scatter distribution is compared to one or more angular distributions scatter calculated for materials of known $Z_{eff}$.

An angular dependence of scatter from a material with a known $Z_{eff}$ is tabulated (808). The angular scatter distributions for a material of a known $Z_{eff}$, θ, and E may be computed based on Equations (1) and (2). These computed distributions may be referred to as calculated angular scatter distributions. The calculated angular scatter distribution may be computed for multiple different materials, each with a different $Z_{eff}$, to generate a table of angular dependence of scattering for materials of various $Z_{eff}$. Alternatively, the calculated angular scatter distribution may be computed for multiple different pure elements, each with a different Z, to generate a table of angular dependence of scattering for each element. A composite material may be expressed in terms of a sum of entries in this table.

The observed scatter data from (802) is compared to the calculated angular scatter distribution (810), and one or more atomic numbers or the $Z_{eff}$ of the object is determined based on the comparison (812). The comparison of the observed x-ray radiation to the table may be performed by statistical tests to determine which computed angular scatter distributions in the table are closest to the observed angular scatter distribution. Because the Z or $Z_{eff}$ of the angular distributions in the table is known, one or more Z or the $Z_{eff}$ of the object may be estimated from the Z or $Z_{eff}$ of the calculated angular scatter distributions that are closest to the observed distributions.

As discussed above, the observed scatter data from (802) may be observed energy dependent scatter data, that is, data that is scatter data measured at a particular angle θ for different x-ray energies E. As an alternative to using the observed angular scatter data, the process 806A may be performed on observed energy dependent scatter data.

Referring to FIG. 8C, another example process for computing the atomic number is shown. FIG. 8C shows an example process 806B that may be used as (806) in the example process 800. The example process 806B uses the total amount of observed scatter over a range of angles to determine the atomic number. For a system that includes multiple detectors, the total amount of observed scatter is the integration or summation of the amount of scatter observed by each detector. The example process 806B may be used to improve results generated from data collected by a system that has relatively coarse angular resolution.

Observed angular scatter data collected in (802) is integrated over the range of observed angles (818). For example, if the scatter data is collected at thirty different detectors, each representing a different scattering angle, the observed angular scatter data may be integrated by summing the observed scatter at each detector. In some implementations, the detectors, each of which represents a particular scattering angle, may be grouped into multiple ranges of angles. For example, and referring briefly to FIG. 5B, the system 500B may include twenty-four detectors 515 that are each positioned at detector positions 514, of which four of the detectors 517 are positioned near 0° and sense primarily coherent scatter 518, and the remaining detectors 519 sense primarily incoherent scatter 520. All, or a subset, of the detectors 517 that are positioned to sense coherent scatter may be integrated to determine an integrated amount for coherent scatter. Similarly, all, or a subset of the detectors 519 positioned to sense incoherent scatter may be integrated to determine an integrated amount for incoherent scatter.

Similar to (808) discussed in FIG. 8B, the angular distribution of scatter may be computed for multiple different materials, each with a different Z or $Z_{eff}$. The computed angular distribution of scatter may be summed or integrated to generate a table of integrated scatter for various Z or $Z_{eff}$. The integrated values of the observed data are compared to the computed values in the table of integrated scatter (820). One or more atomic numbers for the object is determined based on the comparison (822). For example, the one or more atomic numbers or the $Z_{eff}$ of the object may be determined based on the atomic numbers of the computed integrated scattering values in the table that are closest to the observed integrated scattering values.

Figure 10A:
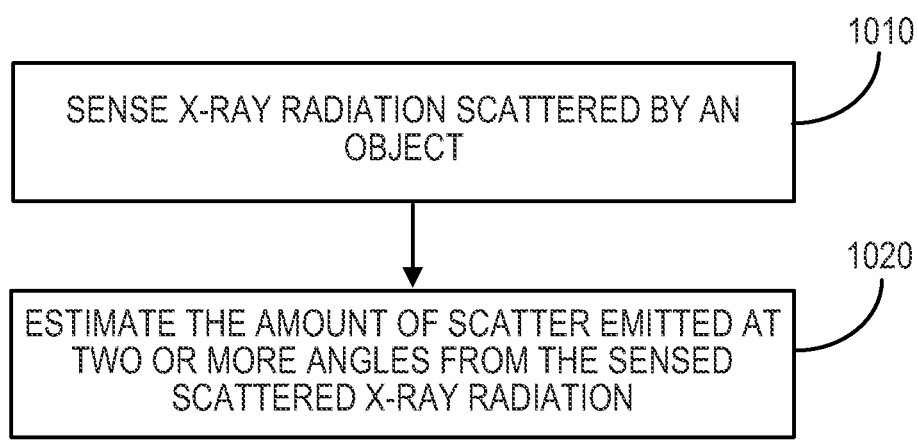
FIG. 10A is a flow chart of another example process for determining a property of a material.

FIG. 10A shows an example process 1000 for determining one or more atomic numbers of an object based on the amount of scatter measured at two or more angles. As illustrated, x-ray radiation scattered by an object (1010) is used to estimate the amount of scatter emitted at two or more angles from the sensed scattered x-ray radiation (1020).

Figure 10B:
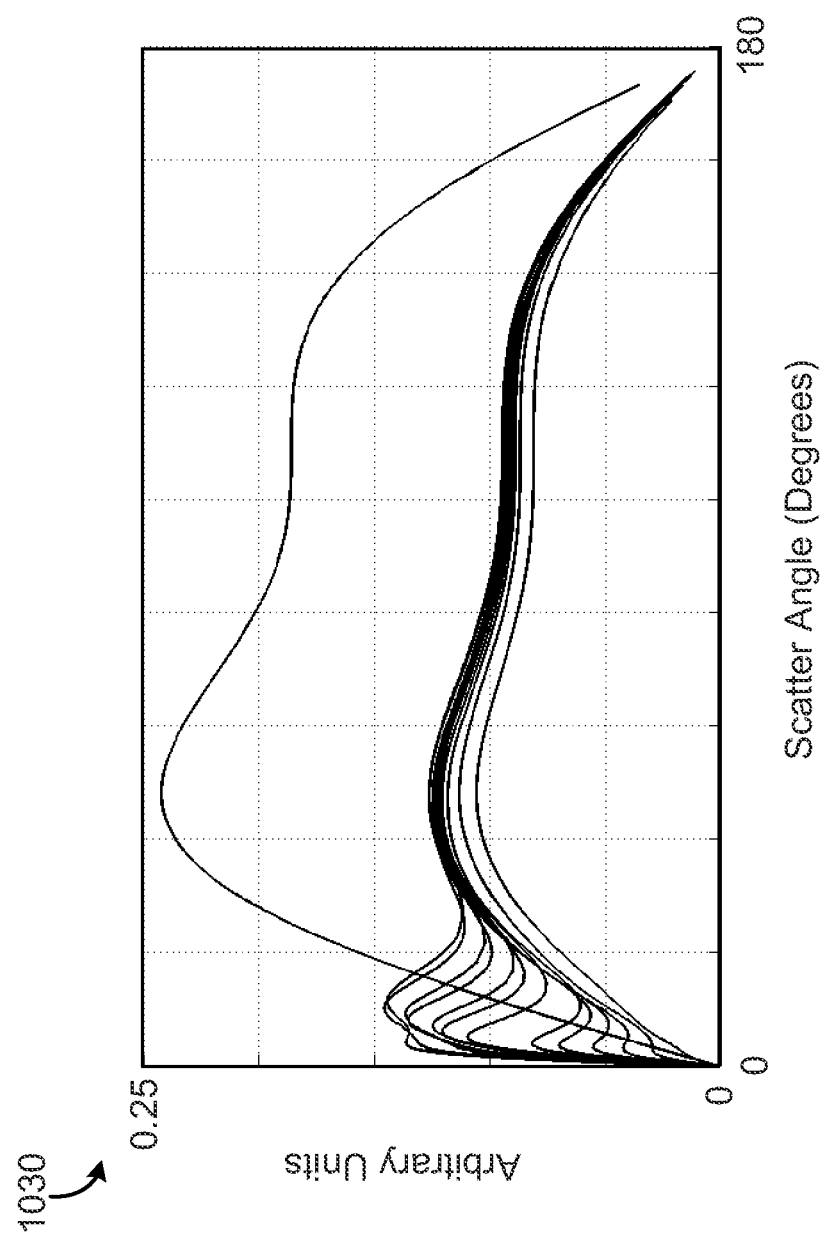
FIG. 10B illustrates example scatter cross-sections that may be used with the process of FIG. 10A.

Referring also to FIG. 10B, an example differential scatter cross-section plot 1030 illustrates a sample functional form of cross-section integrals for various elements. For example, each cross-section may each correspond to H, Li, B, C, N, O, F, Na, Mg, Al, Si, P, S, and Cl. In this example, the scatter cross-sections are weighted by the relative atomic mass of the elements, so as to be able to compare the scatter produced by objects made up of different elements but with identical (macroscopic) densities. The full information of angularly scattered x-rays, as shown in the plot 1030, can be used to yield one or more quantities related to the Z's making up the material. That is, evaluating a shape of the angular distribution or dependence of scatter may yield one or more quantities associated with the object. —For example, ratio(s) of scatter at two or more sets of angles may be used to yield one or more quantities related to the Z's of the material. Alternatively, or additionally, scatter distribution normalized to a single fixed angle, for example 30°, may be used to yield one or more quantities related to the Z's of the material. In some implementations, un-normalized scatter distributions may be used to yield one or more quantities related to the Z's of the material.

Figure 11A:
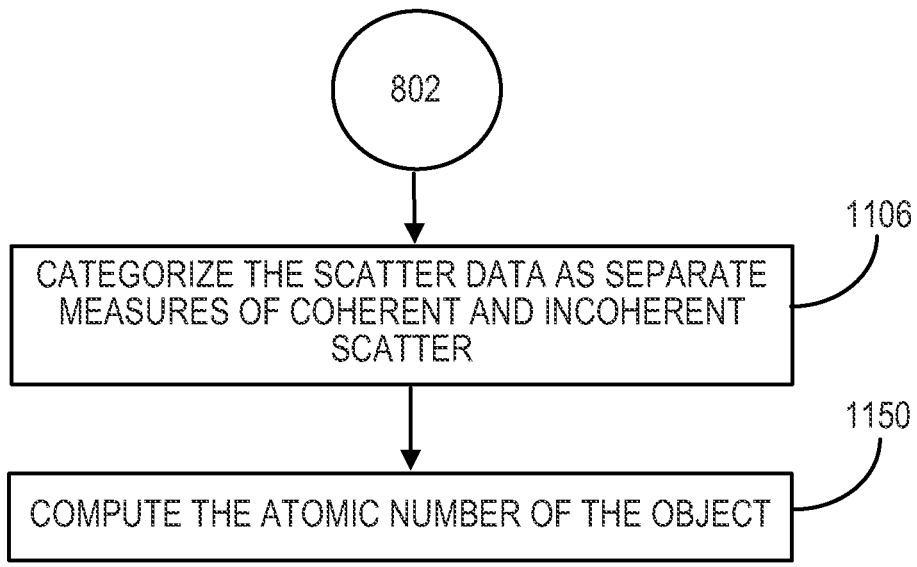
FIG. 11A is a flow chart of another example process for computing the atomic number of the object.
Figure 11B:
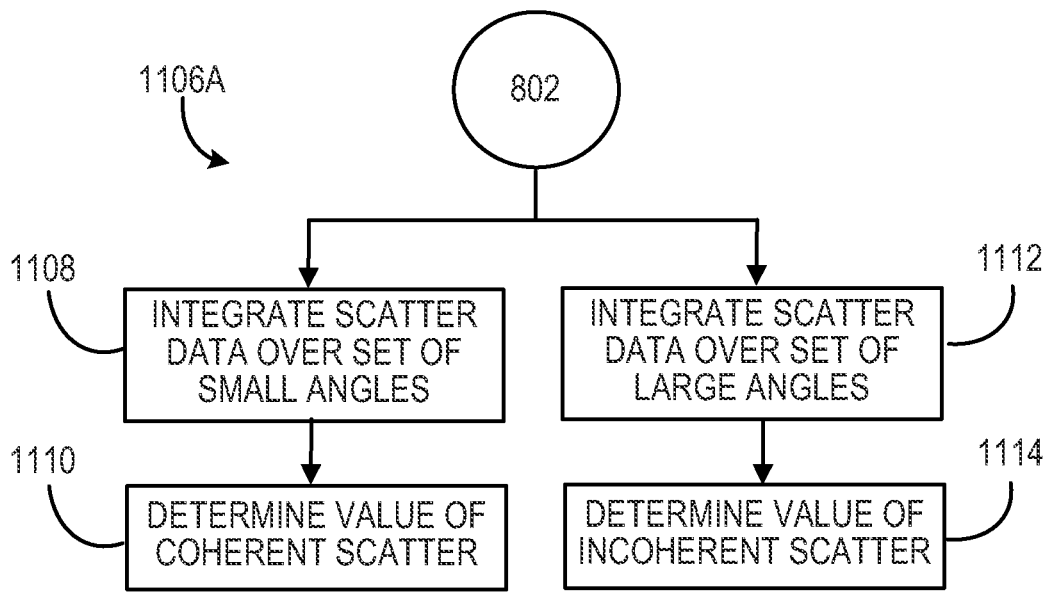
FIGS. 11B-11D are flow charts of example processes for categorizing observed scattered data.
Figure 11C:
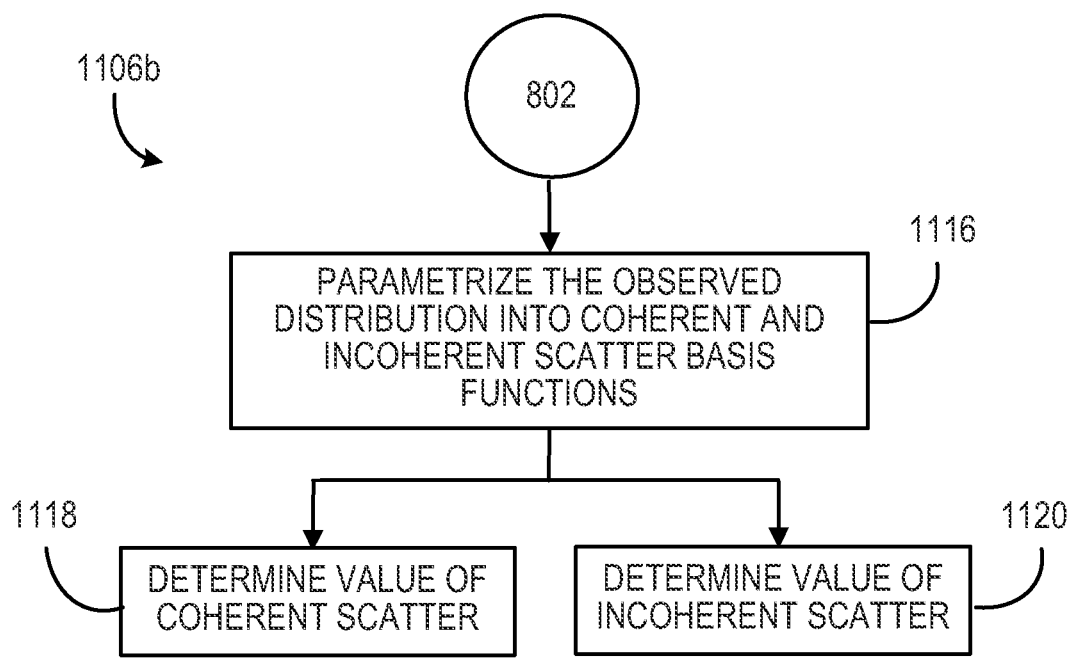
Figure 11D:
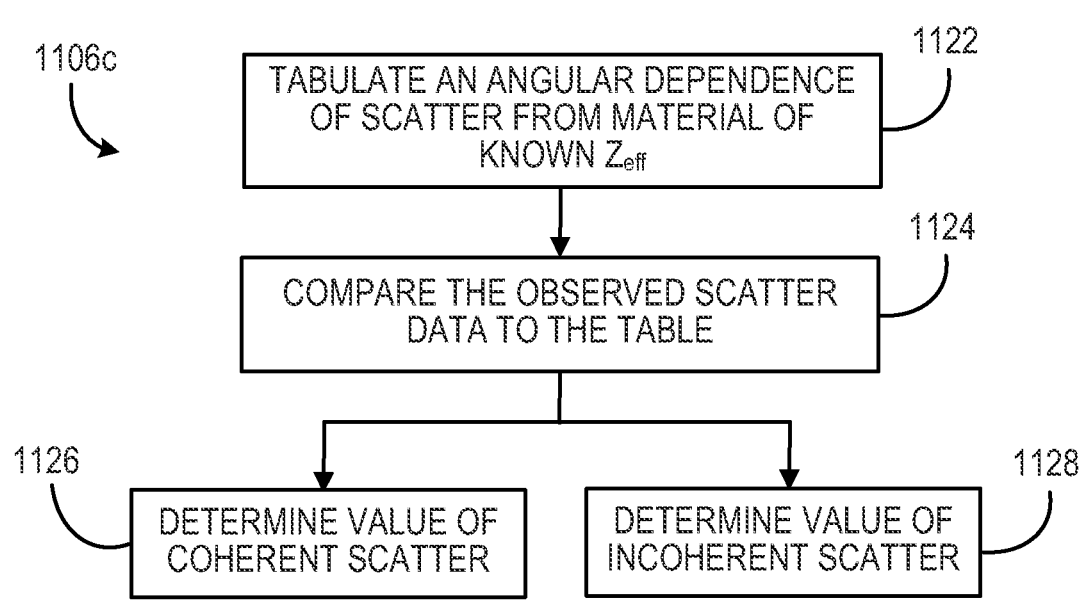
Figure 11E:
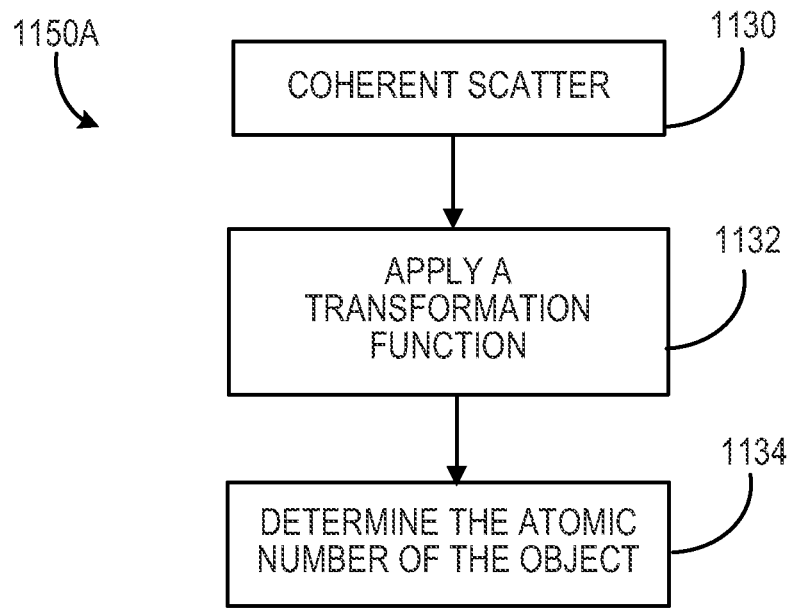
FIGS. 11E-11G are flow charts of example processes for computing the atomic number using categorized scatter data.
Figure 11F:
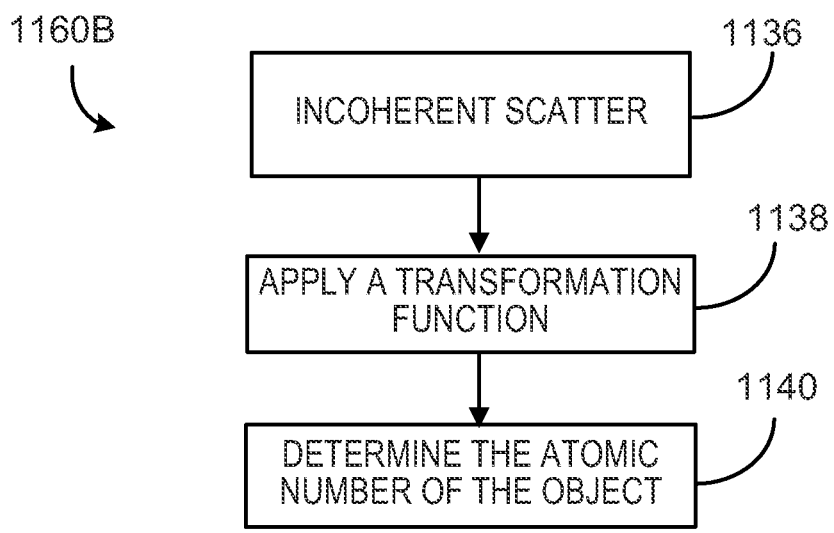
Figure 11G:
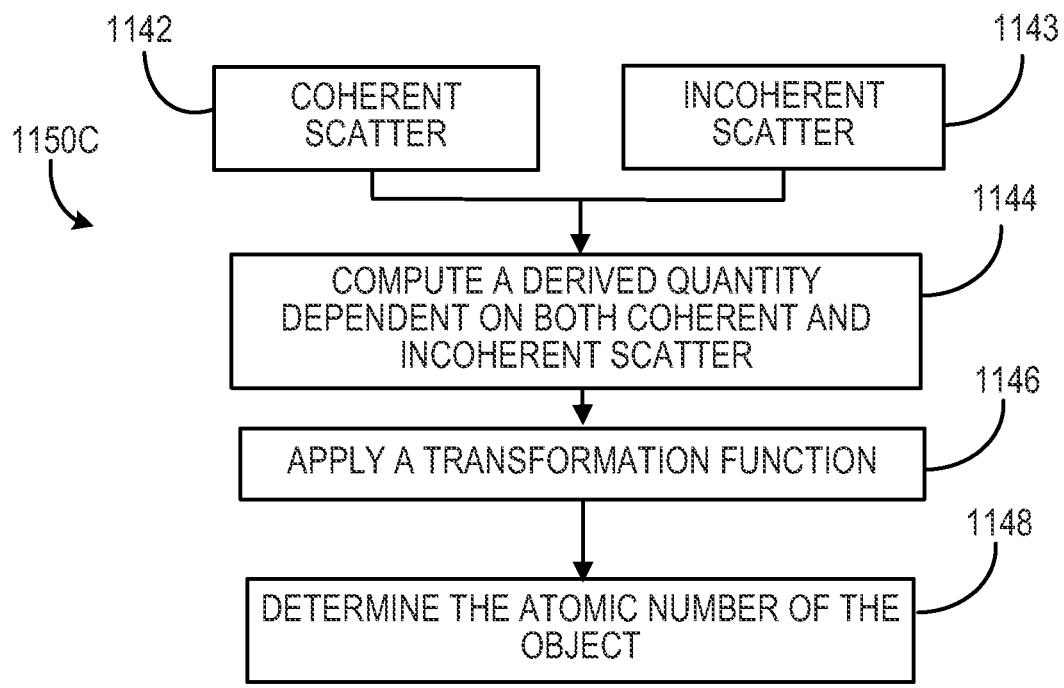

In an alternative implementation, as illustrated in FIG. 11A, another example process 1100 can be used for determining an atomic number of an object. The observed scatter data from (802) is categorized as separate measures of incoherent and coherent scatter (1106). The categorized data is used to compute the atomic number (1150). FIGS. 11B-11D show example processes for categorizing the observed scatter data. FIGS. 11E-11G show example processes for computing the atomic number using the categorized incoherent and/or categorized coherent scatter data.

The techniques discussed in FIGS. 11B-11D use the angular dependence of the scatter to categorize the scatter as coherent or incoherent. As discussed above, coherent scatter tends to be scatter that occurs at smaller scattering angles, whereas incoherent scatter tends to be scatter that occurs at larger scattering angles. Thus, the scattering angle may be used to approximate a category of scatter. Although the techniques discussed below use the angular dependence of scattering, the observed data may additionally or alternatively be categorized by other techniques. For example, incoherent scatter may be estimated based on the total attenuation.

Referring to FIG. 11B, an example process 1106A categorizes observed scatter data as coherent scatter or incoherent scatter. The example process 1106A is based on the angular dependence of scattering and categorizes the observed scatter data by integrating the observed scatter data over a set of small angles associated with coherent scatter and a set of larger angles associated with incoherent scatter.

The observed scatter data is integrated over a set of relatively small scattering angles (1108). The set of relatively small scattering angles may include scattering angles from about 0° to less than about 10° or 20°. Integrating the scatter data over this set of angles provides an estimate of a total amount of coherent scatter. As discussed above, the observed scatter data may be collected by detectors, each of which sense scattering at a different scattering angle. The observed angular scatter data may be integrated over a set of angles by adding the sensed intensity detected by each of the detectors associated with an angle that falls within the range of angles included in the set. A value of coherent scatter is determined from the estimated total (integrated) amount of coherent scatter (1110).

The observed scatter data is integrated over a set of relatively large scattering angles (1112). The relatively large scattering angles may include scattering angles that are, for example, between about 40° and 180°. The observed scatter data may be integrated over the set of relatively large scattering angles in a manner similar to that discussed with respect to the relatively small scattering angles. A value of incoherent scatter is determined from integrating the observed scatter data over the relatively larger scattering angles (1114).

Referring to FIG. 11C, another example process 1106B for categorizing the observed scatter data as incoherent or coherent scatter is shown. In the process 1106B, the observed scatter data is parameterized into coherent and incoherent scatter basis functions (1116). A value of the amount of coherent scatter is determined from the basis functions (1118), and a value of the amount of incoherent scatter is determined from the basis functions (1120).

Referring to FIG. 11D, another example process 1106C for categorizing the observed scatter data as incoherent or coherent scatter is shown. A table including calculated angular distributions of scatter for one or more known materials is generated (1122). The observed scatter data is tested or compared against the calculated distributions (1124). The value of coherent scatter (1126) and incoherent scatter (1128) in the observed scatter data is determined based on the comparison.

FIG. 11E shows an example process 1150A for determining the atomic number of a material using observed data that is categorized as coherent scatter. Data representing coherent scatter is obtained (1130). The data representing coherent scatter may be obtained by any of the categorization techniques discussed above. A transformation function is applied to the coherent scatter data (1132). The transformation function may be a function associated with a material that expresses coherent scatter or the atomic form factor, $F(x,Z)$, as the dependent variable and energy or scattering angle as the independent variable. The atomic number is determined based on the transformation function (1134). An example transformation function is shown in FIG. 11H.

FIG. 11F shows an example process 1150B for determining the atomic number of a material using observed data that is categorized as incoherent scatter. The process 1050B is similar to the process 1150A, except the process 1150B uses incoherent scatter instead of coherent scatter. Data representing incoherent scatter is obtained (1136). The data representing incoherent scatter may be obtained by any of the techniques discussed above. A transformation function is applied to the incoherent scatter data (1138). The transformation function may be a function associated with a material that expresses incoherent scatter or the incoherent scattering factor, $S(x,Z)$, as the dependent variable and energy or scattering angle as the independent variable. An example transformation function is shown in FIG. 11H. The atomic number is determined based on the transformation function (1140).

FIG. 11G shows an example process for determining the atomic number of a material using observed data that is categorized as coherent scatter and incoherent scatter. The example process 1150C obtains the contributions of incoherent scatter (1142) and coherent scatter (1143) from the observed scatter data. The contributions of incoherent and coherent scatter may be obtained by any of the categorizing techniques discussed above. A derived quantity that depends on both the coherent and incoherent scatter is computed (1144). The quantity may be, for example, a ratio of coherent scatter to incoherent scatter. A transformation function that relates the quantity to atomic number is applied to the ratio (1146), and the atomic number is determined from the transformation (1148). An example transformation function is shown in FIG. 11H.

Figure 11H:
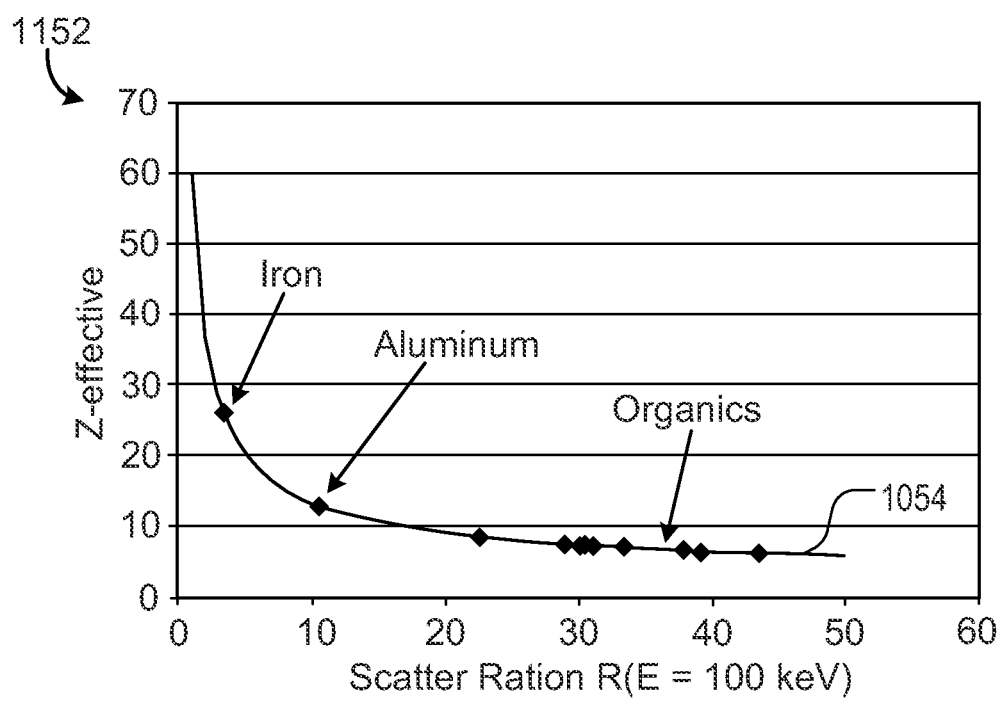
FIG. 11H illustrates an example transformation function that may be used with any of the processes of FIGS. 11E-11G.

FIG. 11H shows an example transformation function that may be applied to a ratio of incoherent to coherent cross-sections, R, to compute the effective atomic number, $Z_{eff}$. The transformation function allows for a determination of $Z_{eff}$ from a measured amount of scatter. For example, values of $Z_{eff}$ and R for known materials (for example, iron, aluminum, and organics) at a known energy level, E, may be obtained and plotted in a plot 1152. A relationship between $Z_{eff}$ and R may then be determined by, for example, fitting the measured data to a function. For example, Equation (4) provides a relationship between $Z_{eff}$ and R for the example shown:

$$Z_{eff}=aR^b+c \qquad (4)$$

where fitting a curve 1154 to the known values of $Z_{eff}$ and R results in $a=57.03$, $b=-0.7266$, and $c=2.56$.

Figure 12:
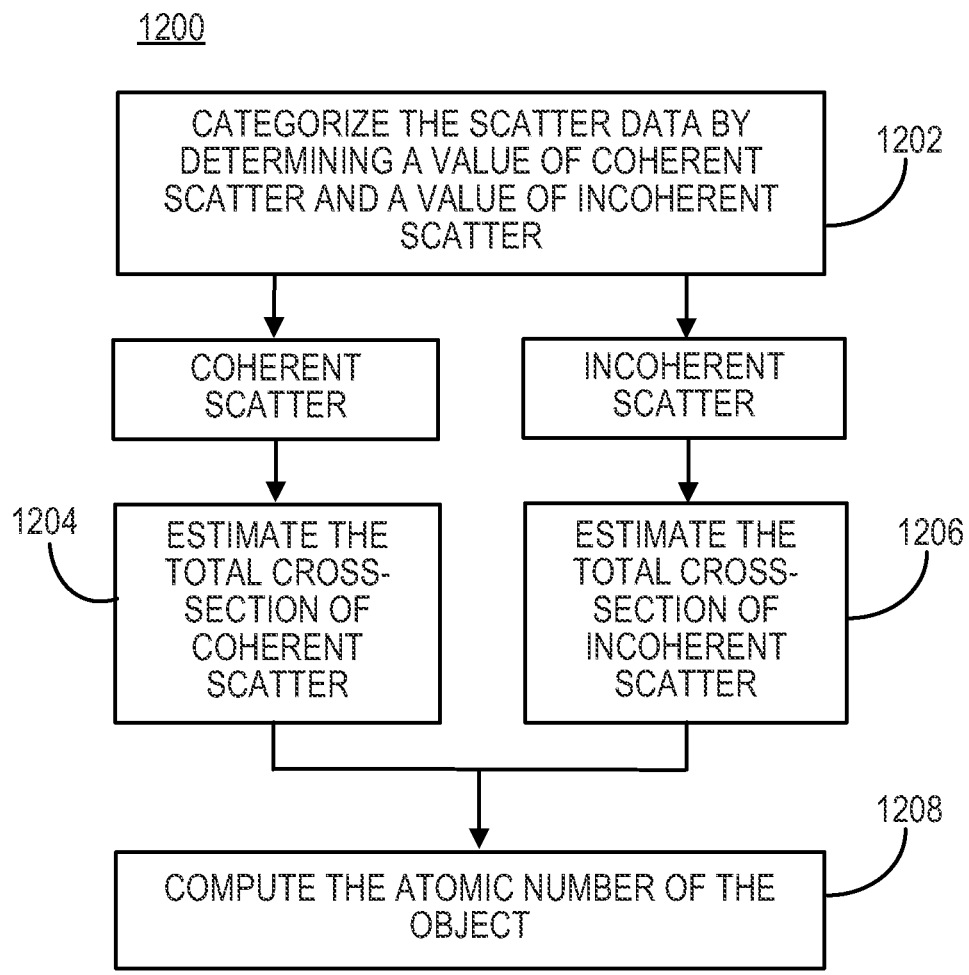
FIG. 12 is a flow chart of another example process for computing the atomic number of the object.

FIG. 12 shows another example process 1200 for computing the atomic number of an object. The example process 1200 is machine-independent. That is, given the same object observed in different scanning machines, the process 1200 produces a consistent, or approximately consistent, estimate for the atomic number of a material of the object.

The geometry of a scanning system may vary depending on the model, manufacturer, or particular configuration of the system. For example, the placement of detectors relative to a space where an object is received and the number of detectors may vary among screening machines. Thus, the range and number of scattering angles at which the scattering is measured may depend on the particular machine that is used to collect the data. However, the total coherent and incoherent scattering cross sections for a particular object may be estimated based on the observed coherent and incoherent angular scattering measured from that object regardless of the geometry in which the observed angular scattering was collected.

The observed scatter data is categorized as coherent scatter or incoherent scatter (1202). The observed scatter data may be categorized as coherent scatter or incoherent scatter using any of the categorizing techniques discussed above. Once the observed scatter data has been categorized as coherent scatter or incoherent scatter, the total cross-section of coherent scatter is estimated from the portion of the observed scatter data that is categorized or identified as coherent scatter (1204), and the total cross-section of incoherent scatter is estimated from the portion of the observed scatter data that is categorized as incoherent scatter (1206). The total cross-section of coherent scatter is an estimate of the probability of x-rays being coherently scattered by the object, and the total cross-section of incoherent scatter is an estimate of the probability of x-rays being incoherently scattered.

The atomic number of the object, or a material that makes up the object, is computed based on the estimates of the total incoherent and coherent cross-sections (1208).

Figure 13:
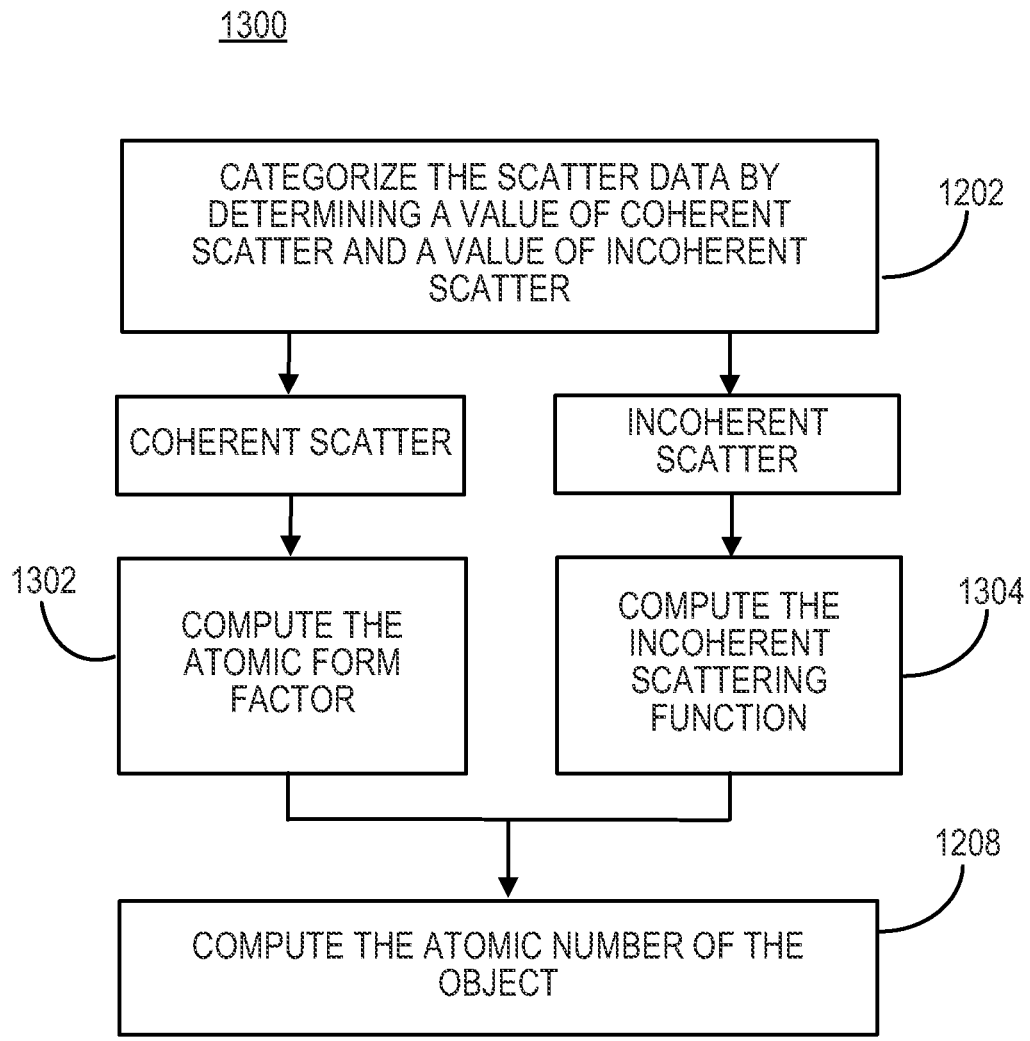
FIG. 13 is a flow chart of an example machine-independent process for computing the atomic number of an object.

FIG. 13 shows another example of a machine-independent process 1300 for computing the atomic number of an object. The example process 1300 is similar to the process 1200, and the observed scatter data is categorized as coherent scatter or incoherent scatter (1202). The observed scatter data may be categorized as coherent scatter or incoherent scatter using any of the categorizing techniques discussed above. However, instead of estimating the total coherent scattering cross-section from observed scatter data that is categorized as coherent, the process 1300 uses this data to compute $F(x,Z)$, the atomic form factor (1302). Additionally, instead of estimating the total incoherent scattering cross-section from the observed scatter data that is categorized as incoherent, the process 1300 uses the incoherent scatter data to compute $S(x,Z)$, the incoherent scattering function (1304).

A number of implementations have been described. Nevertheless, it will be understood that various modifications may be made without departing from the scope of the disclosure. For example, in some implementations, the sensor element 120 of system 100 may be blocked such that the direct beam 106 is not sensed.

What is claimed is:

1. A method comprising:
directing x-ray radiation at an object;
sensing x-ray radiation scattered by the object;
determining an angular distribution of scatter in the sensed scattered radiation relative to a path of the radiation directed at the object;
determining a measurement of a density of the object;
estimating, based on the measurement of the density of the object, an amount of attenuation of the radiation caused by the object;
evaluating the angular distribution based at least on accounting for the estimated amount of attenuation; and
determining one or more atomic numbers, or effective atomic numbers, of materials composing the object based on evaluating the angular distribution.

2. The method of claim 1, wherein evaluating the angular distribution comprises determining a ratio of scatter at two angles.

3. The method of claim 2, wherein determining the one or more atomic numbers, or effective atomic numbers, of materials composing the object comprises determining the one or more atomic numbers, or effective atomic numbers, of materials composing the object based on the ratio of scatter at two angles.

4. The method of claim 3, wherein sensing radiation scatter by the object comprises sensing scattered x-ray radiation at a first angle relative to the path of the radiation directed at the object, the radiation directed at the object being x-ray radiation, and sensing scattered x-ray radiation at a second angle relative to the path of the x-ray beam incident upon the object, the first and second angles being different.

5. The method of claim 4, wherein the object is a homogeneous object comprising a first side and a second side, sensing scattered x-ray radiation at the first angle comprises sensing scattered x-ray radiation on the first side of the object, and sensing scattered x-ray radiation at the second angle comprises sensing scattered x-ray radiation on the second side of the object.

6. The method of claim 4, wherein the first angle indicates a coherent scattering angle, and wherein the second angle indicates an incoherent scattering angle, the second angle being greater than the first angle.

7. The method of claim 3, wherein sensing radiation scattered by the object comprises sensing scattered radiation at two or more distinct angles relative to the path of the radiation that is directed at the object.

8. The method of claim 7, wherein sensing radiation scattered by the object comprises sensing radiation scattered at more than 10 distinct angles, the angles being between about 0 and 180 degrees relative to the path of the radiation directed at the object.

9. The method of claim 7, wherein sensing radiation scattered by the object comprises sensing radiation scattered at more than 30 distinct angles, the angles being between about 0 and 180 degrees relative to the path of the radiation directed at the object.

10. The method of claim 7, wherein a single detector moves relative to the object to sense the scattered radiation at each of the two or more angles.

11. The method of claim 7, further comprising moving a collimator relative to the object, such that the scattered radiation is sensed at the two or more distinct angles when the collimator moves to a position corresponding to the two or more distinct angles.

12. The method of claim 11, wherein the collimator comprises a filter wheel configured to change a path of x-ray radiation relative to the object by moving or rotating.

13. The method of claim 11, wherein collimator comprises a translated opening.

14. The method of claim 1, wherein sensing radiation scattered by the object comprises one or more of measuring x-ray fluency, measuring x-ray energy deposited on a detector, or measuring the x-ray fluency and a per-photon energy.

15. The method of claim 1, wherein sensing scattered radiation comprises sensing, at a single detector, first scattered radiation when a source is in a first position relative to the object, and second scattered radiation when the source is in a second position relative to the object, the first and second positions being different and the first and second scattered radiation being scattered at different angles.

16. The method of claim 1, wherein directing radiation at an object comprises:
generating at least two x-ray beams, each having a distinct energy; and
directing the at least two x-ray beams at the object.

17. The method of claim 1, wherein estimating an amount of attenuation of the radiation caused by the object is further based on a transmission x-ray measurement.

18. The method of claim 17, wherein determining a measurement of a density of the object is based on one or more of computed tomography, a transmission x-ray measurement, measurement of dimensions and weight of the object, or a priori knowledge of a density of the object.

19. The method of claim 1, further comprising presenting a visual representation of the object.

20. A system comprising:
one or more detectors configured to sense x-ray radiation, the detectors being positioned to sense radiation scattered from an object; and
an electronic memory coupled to a processor, the electronic memory comprising instructions that, when executed, cause the processor to:
determine an angular distribution of scatter in the sensed scattered radiation relative to a path of the radiation directed at the object;
determine a measurement of a density of the object;
estimate, based at least on the measurement of the density of the object, an amount of attenuation of the radiation caused by the object;
evaluate the angular distribution based at least on accounting for the estimated amount of attenuation; and
determine a plurality of atomic numbers, or effective atomic numbers, of materials composing the object based on evaluating the angular distribution.

21. The system of claim 20, further comprising one or more sources configured to produce radiation and direct the radiation towards the object.

22. The system of claim 21, wherein the one or more sources are configured to move relative to the object.

23. The system of claim 20, wherein the one or more detectors are configured to move relative to the object.

24. The system of claim 20, further comprising one or more collimating structures located in a path of the radiation scattered from the object.

25. The system of claim 20, wherein determining an angular distribution of scatter comprises one or more of estimating a peak small angle scatter and a peak large angle scatter, estimating an amount of scatter within a range of angles in a small scattering angle region and an amount of scatter within a range of angles in a large scattering angle region, comparing a distribution of the sensed radiation to pre-determined tables, or fitting an angle-dependent distribution of the sensed radiation to a parameterization including both coherent and incoherent contributions.

26. The system of claim 20, wherein the detectors are positioned to sense radiation scattered from an enclosure, the enclosure containing an object.

27. The system of claim 26, wherein the enclosure is a container.

28. The system of claim 27, wherein the container comprises a bottle.

29. The system of claim 26, wherein the enclosure is a pipe, and wherein the object flows through the pipe.

30. The system of claim 26, wherein the enclosure is a tunnel, and wherein the object travels through the tunnel along a conveyor belt.

31. A non-transitory computer-readable medium storing software comprising instructions executable by one or more computers which, upon such execution, cause the one or more computers to perform operations comprising:
directing x-ray radiation at an object;
sensing x-ray radiation scattered by the object;
determining an angular distribution of scatter in the sensed scattered radiation relative to a path of the radiation directed at the object;
determining a measurement of a density of the object;
estimating, based at least on the measurement of the density of the object, an amount of attenuation of the radiation caused by the object;
evaluating the angular distribution based at least on accounting for the estimated amount of attenuation; and
determining one or more atomic numbers, or effective atomic numbers, of materials composing the object based on evaluating the angular distribution.

* * * * *